United States Patent
Kawabata et al.

(10) Patent No.: US 11,479,537 B2
(45) Date of Patent: Oct. 25, 2022

(54) T-TYPE CALCIUM CHANNEL INHIBITOR

(71) Applicants: KINKI UNIVERSITY, Higashiosaka (JP); NATIONAL UNIVERSITY CORPORATION UNIVERSITY OF TOYAMA, Toyama (JP); FUSO PHARMACEUTICAL INDUSTRIES, LTD., Osaka (JP)

(72) Inventors: Atsufumi Kawabata, Higashiosaka (JP); Fumiko Sekiguchi, Higashiosaka (JP); Maho Tsubota, Higashiosaka (JP); Naoki Toyooka, Toyama (JP); Hiroyuki Nishikawa, Osaka (JP)

(73) Assignees: KINKI UNIVERSITY, Osaka (JP); NATIONAL UNIVERSITY CORPORATION UNIVERSITY OF TOYAMA, Toyama (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/650,746
(22) PCT Filed: Sep. 21, 2018
(86) PCT No.: PCT/JP2018/035170
§ 371 (c)(1),
(2) Date: Mar. 25, 2020
(87) PCT Pub. No.: WO2019/065532
PCT Pub. Date: Apr. 4, 2019

(65) Prior Publication Data
US 2020/0308132 A1   Oct. 1, 2020

(30) Foreign Application Priority Data
Sep. 28, 2017 (JP) .............. JP2017-188717

(51) Int. Cl.
C07D 311/32 (2006.01)
A61P 23/00 (2006.01)

(52) U.S. Cl.
CPC .......... *C07D 311/32* (2013.01); *A61P 23/00* (2018.01)

(58) Field of Classification Search
CPC ................ C07D 311/32; A61P 23/00
See application file for complete search history.

(56) References Cited

U.S. PATENT DOCUMENTS

| 2003/0180394 A1 | 9/2003 | Erdelmeier et al. |
| 2018/0065947 A1 | 3/2018 | Kawabata et al. |

FOREIGN PATENT DOCUMENTS

| CN | 106518629 | * 3/2017 | ............. C07C 39/21 |
| JP | 3327699 | 9/2002 | |
| JP | 4393062 | 1/2010 | |
| WO | 2014/188980 | 11/2014 | |

OTHER PUBLICATIONS

Machine translation of CN 106518629, Accessed May 22, 2021, Obtained from worldwide.espacenet.com.*
Kaulich et al., Drug Development Research, 59:72-81 (2003).*
Todorovic et al., "Redox Modulation of T-Type Calcium Channels in Rat Peripheral Nociceptors," Neuron, 2001, 31(1), p. 75-85.
Huang et al., "NNC 55-0396 [(1S,2S)-2-(2-(N-[(3-Benzimidazol-2-yl)propyl]-Nmethylamino)ethyl)-6-fluoro-1,2,3,4-tetrahydro-1-isopropyl-2-naphtyl cyclopropanecarboxylate dihydrochloride]: A New Selective Inhibitor of T-Type Calcium Channels," J Pharmacol Exp Ther., 2004, 309(1), p. 193-199.
Ye et al., "Identification and Enrichment of α-Glucosidase-Inhibiting Dihydrostilbene and Flavonoids from Glycyrrhiza uralensis Leaves," Journal of Agricultural and Food Chemistry, Dec. 26, 2016, 65, pp. 510-515, <DOI: 10.1021/acs.jafc.6604155>, [retrieved on Nov. 22, 2018].
Nguyen et al., "Design and synthesis of novel anti-hyperalgesic agents based on 6-prenylnaringenin as the T-type calcium channel blockers," Bioorganic & Medicinal Chemistry, Jul. 19, 2018,26, pp. 4410-4427, <DOI:10.1016/j.bmc.2018.07.023>, [retrieved on Nov. 22, 2018].
International Search Report of PCT/JP2018/035170, Dec. 4, 2018, 4 pages including English translation.

\* cited by examiner

*Primary Examiner* — Alicia L Otton
(74) *Attorney, Agent, or Firm* — Hamre, Schumann, Mueller & Larson, P.C.

(57) ABSTRACT

A new analgesic has been developed for T-type calcium channels as therapeutic targets.
The present invention provides a T-type calcium channel inhibitor which is a compound represented by formula (1):

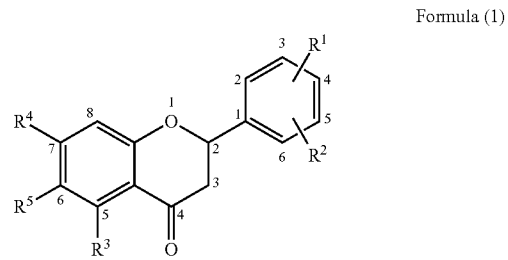

Formula (1)

wherein
each of $R^1$ and $R^2$ independently represents —H or —OH;
$R^3$ represents —OH;
$R^4$ represents —OH or —H;
$R^5$ represents a straight or branched alkyl or cycloalkyl-alkyl group having one to ten carbon atoms or a straight or branched alkenyl or cycloalkyl-alkenyl group having two to ten carbon atoms,
or a pharmaceutically acceptable salt or solvate thereof.
The present invention also provides this T-type calcium channel inhibitor, a medicament containing the T-type calcium channel inhibitor, and a therapeutic or prophylactic agent for a disease having an effective T-type calcium channel inhibitory action.

8 Claims, 5 Drawing Sheets

Fig. 2

**P<0.001 vs. SHAM OPERATION + SOLVENT
†P<0.05、††P<0.01 vs. PNSL + SOLVENT

Fig. 4

**P<0.001 vs. SHAM OPERATION + SOLVENT
†P<0.05、††P<0.01 vs. PNSL + SOLVENT

Fig. 5

**P<0.001 vs. SHAM OPERATION + SOLVENT
†P<0.05、††P<0.01 vs. PNSL + SOLVENT

T-TYPE CALCIUM CHANNEL INHIBITOR

TECHNICAL FIELD

The present invention relates to a T-type calcium channel inhibitor which is a flavanone compound. The present invention also relates to a pharmaceutical product containing the T-type calcium channel inhibitor, and a therapeutic agent or prophylactic agent for diseases, the effective action of which is a T-type calcium channel inhibitory action.

BACKGROUND ART

Ion channels are channels extending through the cell membrane, and are classified broadly into two types: ligand-dependent channels and potential-dependent channels. In recent years, as a type of mechanism of neuropathic pains, a potential-dependent sodium channel and a potential-dependent calcium channel have been found as a target. As drugs targeting a potential-dependent sodium channel, for example, lidocaine, carbamazepine, lamotrigine, mexiletine and the like are known. As drugs targeting a potential-dependent calcium channel, for example, gabapentin, pregabalin, ziconotide and the like are known.

The neuropathic pain is refractory, and has the problem of inadequate response to existing analgesic drugs. The efficacy of even an established drug therapy is difficult to predict accurately, and other drugs must often be used in combination. In "Guidelines for the Pharmacologic Management of Neuropathic Pain" from Japan Society of Pain Clinicians, high-potential-activated calcium channel inhibitors are listed as a primary choice, but in many cases, an adequate therapeutic effect is not obtained. These inhibitors have a problem of causing side effects such as lightheadedness.

Potential-dependent calcium channels are classified into two types: high-potential-activated types and low-potential-activated types based on a difference in activation and deactivation potentials. L-type, N-type, P/Q-type and R-type calcium channels are activated by large depolarization, and therefore classified as high-potential-activated calcium channels. On the other hand, T-type calcium channels are activated by small depolarization, and therefore classified as low-potential-activated calcium channels.

Recently, T-type calcium channels have been reported to be involved in onset and development of a neuropathic pain, and potential of T-type calcium channel inhibitors as therapeutic agents for the neuropathic pain has been suggested. Examples of the T-type calcium channel inhibitor include mibefradil (see, for example, Todorovic, Neuron, 2001, 31 (1), p. 75-85 (Non-Patent Document 1)), ethosuximide, and (1S,2S)-2-[2-[[3-(1H-benzimidazol-2-yl)propyl] methyamino]ethyl]-6-fluoro-1,2,3,4-tetrahydro-1-(1-methylethyl)-2-naphthalenyl-cyclopropane carboxylate hydrochloride (NNC55-0396)(see, for example, Huang, J Pharmacol Exp Ther., 309 (1), p. 193-199 (Non-Patent Document 2)). Thus, some compounds have already been found as T-type calcium channel inhibitors, but further studies on new T-type calcium channel inhibitors are required in view of side effects etc.

Flavanone compounds having a flavanone backbone are compounds contained in natural extracts etc. These flavanone compounds have been found to have various drug efficacies. For example, it has been found that sophoraflavanone G which is a type of flavanone compound can be used as an antibacterial agent having an inhibitory action on proliferation of Propionibacterium acnes and Pityrosporum ovale (Japanese Patent No. 3327699 (Patent Document 1)). For example, Japanese Patent No. 4393062 (Patent Document 2) discloses that extracts from Sophora, which contain a flavone selected from the group consisting of 8-prenylnaringenin, kushenol X, 8-prenylkaempferol, leachianone G and kushenol E, an alkaloid, an isoflavone, a chalcone and a pterocarpan are capable of preventing and treating disease conditions caused by abnormal metabolism of estrogen. On the other hand, it is not disclosed that the flavanone compound has a T-type calcium channel inhibitory action. In addition, WO 2014/188980 (Patent Document 3) discloses a T-type calcium channel inhibitor which has a flavanone structure, a pharmaceutical composition containing the same, and a therapeutic agent or prophylactic agent for diseases for which T-type calcium channel inhibition action is effective. However, this prior art document comprehensively discloses compounds having a flavanone structure but does not disclose that particular compounds of the present invention actually exhibit a T-type calcium channel inhibition effect.

PRIOR ART DOCUMENTS

Patent Documents

Patent Document 1: Japanese Patent No. 3327699
Patent Document 2: Japanese Patent No. 4393062
Patent Document 3: WO 2014/188980
Non-Patent Document 1: Todorovic, Neuron, 2001, 31(1), p. 75-85.
Non-Patent Document 2: Huang, J Pharmacol Exp Ther., 2004, 309(1), p. 193-199.

SUMMARY OF INVENTION

Problem to be Solved by the Invention

The present inventors have searched for a new T-type calcium channel inhibitor towards development of a new analgesic drug targeting a T-type calcium channel for therapeutic. As a result, the present inventors have found that a particular flavanone compound strongly inhibits a T-type calcium channel, leading to completion of the present invention.

An object of the present invention is to provide a T-type calcium channel inhibitor which is a flavanone compound; a pharmaceutical product containing the T-type calcium channel inhibitor; and a therapeutic agent or prophylactic agent for diseases, the effective action of which is a T-type calcium channel inhibitory action.

Means for Solving the Problem

The present invention provides a T-type calcium channel inhibitor, wherein the T-type calcium channel inhibitor is a compound represented by the formula (1):

Formula (1)

[wherein each of $R^1$ and $R^2$ independently represents H or —OH,
$R^3$ represents —OH,
$R^4$ represents —OH or —H, R⁵ represents a straight or branched alkyl or cycloalkyl-alkyl group having one to ten carbon atoms or a straight or branched alkenyl or cycloalkyl-alkenyl group having two to ten carbon atoms], a pharmaceutically acceptable salt of the compound, a solvate of the compound, or an analgesic containing these compounds. The above-mentioned object is hereby achieved.

In addition, among the compounds represented by the formula (1), following compounds are particularly preferable:

5,7-dihydroxy-2-(2-hydroxy-phenyl)-6-(3-methyl-but-2-enyl)-chroman-4-one (Compound-33);
5,7-dihydroxy-2-(3-hydroxy-phenyl)-6-(3-methyl-but-2-enyl)-chroman-4-one (Compound-34);
2-(3,4-dihydroxy-phenyl)-5,7-dihydroxy-6-(3-methyl-but-2-enyl)-chroman-4-one (Compound-36);
5,7-dihydroxy-2-(4-hydroxy-phenyl)-6-(3-methyl-butyl)-chroman-4-one (Compound-39);
6-(3-ethyl-pent-2-enyl)-5,7-dihydroxy-2-(4-hydroxy-phenyl)-chroman-4-one (Compound-40);
6-(2-cyclopentylidene-ethyl)-5,7-dihydroxy-2-(4-hydroxy-phenyl)-chroman-4-one (Compound-41);
2-(2,6-dihydroxy-phenyl)-5,7-dihydroxy-6-(3-methyl-but-2-enyl)-chroman-4-one (Compound-42);
5-hydroxy-2-(2-hydroxy-phenyl)-6-(3-methyl-but-2-enyl)-chroman-4-one (Compound-43);
6-(3-ethyl-pent-2-enyl)-5,7-dihydroxy-2-(2-hydroxy-phenyl)-chroman-4-one (Compound-45);
6-(3-ethyl-pentyl)-5,7-dihydroxy-2-(4-hydroxy-phenyl)-chroman-4-one (Compound-46);
6-(2-cyclopentyl-ethyl)-5,7-dihydroxy-2-(4-hydroxy-phenyl)-chroman-4-one (Compound-47); and
5,7-dihydroxy-2-(4-hydroxy-phenyl)-6-(3-propyl-hex-2-enyl)-chroman-4-one (Compound-48).

Further, among the compounds represented by the general formula (1), the following compounds are more preferable.
6-(3-ethyl-pent-2-enyl)-5,7-dihydroxy-2-(4-hydroxy-phenyl)-chroman-4-one (Compound-40);
6-(2-cyclopentylidene-ethyl)-5,7-dihydroxy-2-(4-hydroxy-phenyl)-chroman-4-one (Compound-41);
6-(3-ethyl-pent-2-enyl)-5,7-dihydroxy-2-(2-hydroxy-phenyl)-chroman-4-one (Compound-45); and
6-(2-cyclopentyl-ethyl)-5,7-dihydroxy-2-(4-hydroxy-phenyl)-chroman-4-one (Compound-47).

The present invention also provides a pharmaceutical product containing the above-mentioned T-type calcium channel inhibitor, and a therapeutic agent or prophylactic agent for neuropathic pain containing the above-mentioned T-type calcium channel inhibitor.

Effect of the Invention

The T-type calcium channel inhibitor according to the present invention which is a flavanone compound has an excellent T-type calcium channel inhibitory action. The T-type calcium channel inhibitor according to the present invention is very useful in the fields of, for example, medical cares, pharmaceutical products and prophylactic agents.

BRIEF DESCRIPTION OF DRAWINGS

FIG. 2 is a graph chart showing the inhibitory action of Compound-40 on partial sciatic nerve ligation (PSNL)-induced hyperalgesia. Open circles show a result of vehicle administration after sham operation, open upward triangles show a result of vehicle administration after PSNL-induced hyperalgesia, open diamonds show a result of 6-prenylnaringenin 10 mg/kg administration after PSNL-induced hyperalgesia, open squares show a result of 6-prenylnaringenin 20 mg/kg administration after PSNL-induced hyperalgesia, open downward triangles show a result of 6-prenylnaringenin 30 mg/kg administration after PSNL-induced hyperalgesia, solid diamonds show a result of Compound-40 10 mg/kg administration after PSNL-induced hyperalgesia, and solid downward triangles show a result of Compound-40 30 mg/kg administration after PSNL-induced hyperalgesia.

MODE FOR CARRYING OUT THE INVENTION

The T-type calcium channel inhibitor according to the present invention has a structure represented by the following Formula (1).

Formula (1)

In the formula (1),
each of $R^1$ and $R^2$ independently represents H or —OH;
$R^3$ represents —OH;
$R^4$ represents —OH or H; and
$R^5$ represents a straight or branched alkyl or cycloalkyl-alkyl group having one to ten carbon atoms or a straight or branched alkenyl or cycloalkyl-alkenyl group having two to ten carbon atoms.

Among the compounds represented by the formula (1),
5,7-dihydroxy-2-(2-hydroxy-phenyl)-6-(3-methyl-but-2-enyl)-chroman-4-one (Compound-33);
5,7-dihydroxy-2-(3-hydroxy-phenyl)-6-(3-methyl-but-2-enyl)-chroman-4-one (Compound-34);
2-(3,4-dihydroxy-phenyl)-5,7-dihydroxy-6-(3-methyl-but-2-enyl)-chroman-4-one (Compound-36);
5,7-dihydroxy-2-(4-hydroxy-phenyl)-6-(3-methyl-butyl)-chroman-4-one (Compound-39);
6-(3-ethyl-pent-2-enyl)-5,7-dihydroxy-2-(4-hydroxy-phenyl)-chroman-4-one (Compound-40);
6-(2-cyclopentylidene-ethyl)-5,7-dihydroxy-2-(4-hydroxy-phenyl)-chroman-4-one (Compound-41);
2-(2,6-dihydroxy-phenyl)-5,7-dihydroxy-6-(3-methyl-but-2-enyl)-chroman-4-one (Compound-42);
5-hydroxy-2-(2-hydroxy-phenyl)-6-(3-methyl-but-2-enyl)-chroman-4-one (Compound-43);
6-(3-ethyl-pent-2-enyl)-5,7-dihydroxy-2-(2-hydroxy-phenyl)-chroman-4-one (Compound-45);
6-(3-ethyl-pentyl)-5,7-dihydroxy-2-(4-hydroxy-phenyl)-chroman-4-one (Compound-46);
6-(2-cyclopentyl-ethyl)-5,7-dihydroxy-2-(4-hydroxy-phenyl)-chroman-4-one (Compound-47); and
5,7-dihydroxy-2-(4-hydroxy-phenyl)-6-(3-propyl-hex-2-enyl)-chroman-4-one (Compound-48) are preferable.

In addition, among the compounds represented by the formula (1),
6-(3-ethyl-pent-2-enyl)-5,7-dihydroxy-2-(4-hydroxy-phenyl)-chroman-4-one (Compound-40);
6-(2-cyclopentylidene-ethyl)-5,7-dihydroxy-2-(4-hydroxy-phenyl)-chroman-4-one (Compound-41);
6-(3-ethyl-pent-2-enyl)-5,7-dihydroxy-2-(2-hydroxy-phenyl)-chroman-4-one (Compound-45); and
6-(2-cyclopentyl-ethyl)-5,7-dihydroxy-2-(4-hydroxy-phenyl)-chroman-4-one (Compound-47) are more preferable.

Further, among these compounds, Compound-40, Compound-41, Compound-45 and Compound-47 are particularly preferable since these Compounds have a higher effect.

In the T-type calcium channel inhibitor represented by the above formula (1) according to the present invention, the compound represented by the above formula (1) may be in the form of a salt. That is, a pharmaceutically acceptable salt of the compound represented by the above formula (1) can also be used as a T-type calcium channel inhibitor. Examples of the pharmaceutically acceptable salt include hydrochlorides, sulfates, methanesulfonates, hydrobromates, acetates, benzoates, tartrates, lactates, malates, salicylates, phosphates, maleates, fumarates etc.

In the T-type calcium channel inhibitor represented by the above formula (1) according to the present invention, the compound represented by the above formula (1) may be in the form of a solvate. The solvate is not particularly limited as long as it is pharmaceutically acceptable, and examples thereof may include hydrates, and alcoholates such as ethanolates.

The T-type calcium channel inhibitors according of the present invention also include prodrugs of the T-type calcium channel inhibitor represented by the above formula (1). The term "prodrug" means a compound which is converted into an activated form having a pharmacological action by hydrolysis in the body, for example, in blood. Examples of the pharmacologically acceptable prodrug are described in the documents: T. Higuchi and V. Stella, Prodrugs as Novel Drug Delivery Systems, "Bioreversible Carriers in Drug Design," edited by Edward B. Roche, American Pharmaceutical Association and Pergamon Press, A.C.S. Symposium Series, Vol. 14, (1987); and D. Fleisher, R. Bong and B. H. Stewart, "Improved oral drug delivery: Solubility limitations overcome by the use of prodrugs," Advanced Drug Delivery Reviews (1996), 19(2):115-130. When the compound represented by the formula (1) has a hydroxyl group, examples of the prodrug include prodrugs such as acyloxy derivatives which are prepared by reacting an acyl halide, an acid anhydride or a halogenated alkyloxy carbonyl compound with the compound represented by the formula (1).

A therapeutic agent or prophylactic agent for diseases according to the present invention, the effective action of which is a T-type calcium channel inhibitory action, can be administered as an orally-administered agent such as a general tablet, capsule, powder, granule, pill or oral liquid (syrup), a transmucosal absorption agent such as a renal administration agent, a nasal absorption agent or a transvaginal absorption agent, a pulmonary absorption agent, an inhalant, an eye drop, a transdermal absorption agent, or an injection. In the therapeutic agent or prophylactic agent according to the present invention, the T-type calcium channel inhibitor according to the present invention may be used as a single therapeutic agent, or may be used as a mixture with other therapeutic agents. In administration, the T-type calcium channel inhibitor is generally administered as a pharmaceutical composition.

The therapeutic agent or prophylactic agent according to the present invention can be produced by a method commonly known by those skilled in the art using pharmacologically and pharmaceutically acceptable additives as necessary. For example, in the case of a tablet, a capsule or a granule, the therapeutic agent or prophylactic agent can be prepared using additives that are usually used, such as an excipient, a lubricant, a binder, a disintegrator, a wetting agent, a plasticizer and a coating agent. The oral liquid may be in the form of an aqueous or oily suspension, a solution, an emulsion, a syrup or an elixir, or may be provided as a dry syrup which is formulated into an oral liquid with water or any other suitable solvent before use. Such an oral liquid can be prepared using additives that are usually used, such as a suspending agent, a flavor, a diluent and an emulsifier.

The suppository can be prepared using additives such as an emulsifier, a suspending agent and a preservative as necessary with a suitable substance as a base, such as cocoa butter, laurin butter, macrogol, glycerogelatin, witepsol, sodium stearate or a mixture thereof. The injection can be prepared using a resolvent such as distilled water for injection, physiological saline, a 5% glucose solution or propylene glycol, and additives as necessary such as a solubilizer, a pH regulator, an isotonizing agent and a stabilizer.

When the T-type calcium channel inhibitor according to the present invention is administered to a human, the dose can be adjusted according to the age and conditions of a patient to which the inhibitor is administered. When the patient is an adult, normally the dose is generally about 0.1 to 1000 mg/person/day in the case of an oral agent or intrarectal administration, and generally about 0.05 mg to 500 mg/person/day in the case of an injection. These values are merely illustrative, and the dose of the agent is determined in accordance with conditions etc. of the patient.

The therapeutic agent or prophylactic agent for diseases according to the present invention, the effective action of which is a T-type calcium channel inhibitory action, is, for example, a therapeutic agent or prophylactic agent for neuropathic pains. The therapeutic agent or prophylactic agent for diseases according to the present invention, the effective action of which is a T-type calcium channel inhibitory action, is not limited to the therapeutic agent or prophylactic agent for neuropathic pains. Other therapeutic agents or prophylactic agents for diseases according to the present invention, the effective action of which is a T-type calcium channel inhibitory action, include, for example, therapeutic agents or prophylactic agents for epilepsy, therapeutic agents or prophylactic agents for hyperaldosteronemia, therapeutic agents or prophylactic agents for inflammation, therapeutic agents or prophylactic agents for edemas, therapeutic agents or prophylactic agents for cardiac hypertrophy, therapeutic agents or prophylactic agents for heart failure, therapeutic agents or prophylactic agents for cardiomyopathy, therapeutic agents or prophylactic agents for atrial fibrillation, therapeutic agents or prophylactic agents for tachyarrhythmia, therapeutic agents or prophylactic agents for arteriosclerosis, therapeutic agents or prophylactic agents for nephritis, therapeutic agents or prophylactic agents for renal disorders and therapeutic agents or prophylactic agents for renal failure.

All the publications, patents and patent applications cited herein are incorporated herein by reference in their entirety.

EXAMPLES

The present invention will be described further in detail by way of examples below, but the present invention is not limited to these examples. In examples, "%" is on a weight basis unless otherwise specified.

Preparation Example: Preparation of Compounds

SYNTHESIS OF COMPOUNDS-39 TO 41 AND 46 TO 48

COMPOUND-39: R = Me (100%)
COMPOUND-48: R = Et (100%)
COMPOUND-47: R—R = cyclopentyl (100%)

Compounds-39 to 41 and Compounds-46 to 48 were synthesized according to above Scheme 1.

Under Ar atmosphere, an olefin (5.00 mmol), Grubbs catalyst and 2nd Generation (0.012 mmol) were sequentially added to a solution of acetic acid 4-(7-acetoxy-6-allyl-5-hydroxy-4-oxo-chroman-2-yl)-phenyl ester $1^1$ (0.25 mmol) in benzene (5 mL) at room temperature, and the mixture was heated at 100° C. for 12 hours in a sealed tube. After cooling, the solvent was distilled off, and the obtained residue was purified by silica gel column chromatography (hexane: EtOAc=10:1 (volume ratio))(Rf value=0.25 by thin-layer chromatography) to obtain yellow crystals (2a) to (2c). The physical properties of the obtained intermediate compounds (2a) to (2c) were as follows.

Acetic acid 4-[7-acetoxy-6-(3-ethyl-pent-2-enyl)-5-hydroxy-4-oxo-chroman-2-yl]-phenyl Ester (2a)

$^1$H-NMR (400 MHz CDCl$_3$) δ:0.96 (3H, t, J=7.2 Hz), 1.03 (3H, t, J=7.2 Hz), 2.00 (2H, q, J=7.2 Hz), 2.20 (2H, q, J=7.2 Hz), 2.29 (3H, s), 2.31 (3H, s), 2.85 (1H, dd, J=17.2, 2.8 Hz), 3.08 (1H, dd, J=17.2, 13.2 Hz), 3.26 (2H, d, J=7.2 Hz), 5.04 (1H, t, J=7.2 Hz), 5.43 (1H, dd, J=13.2, 2.8 Hz), 6.28 (1H, s), 7.15 (2H, d, J=8.4 Hz), 7.45 (2H, d, J=8.4 Hz), 12.17 (1H, s); $^{13}$C-NMR (100 MHz CDCl$_3$) δ:12.55, 13.05, 20.89, 21.07, 21.37, 23.25, 29.02, 43.69, 78.49, 102.06, 106.14, 115.31, 119.23, 122.02, 127.25, 135.71, 143.40, 150.85, 156.55, 159.57, 161.23, 168.35, 169.29, 197.01; IR (neat): 2964, 1769, 1752, 1646, 1633, 1585, 1511, 1431, 1371, 1303, 1219, 1193, 1141, 1086, 1065, 900 cm$^{-1}$; mp: 70-72° C.

Acetic acid 4-[7-acetoxy-5-hydroxy-4-oxo-6-(3-propyl-hex-2-enyl)-chroman-2-yl]-phenyl Ester (2b)

$^1$H-NMR (400 MHz CDCl$_3$) δ:0.82 (3H, t, J=7.2 Hz), 0.93 (3H, t, J=7.2 Hz), 1.28-1.45 (4H, m), 1.90 (2H, t, J=7.2 Hz), 2.11 (2H, t, J=7.2 Hz), 2.27 (3H, s), 2.30 (3H, s), 2.79 (1H, dd, J=17.2, 2.8 Hz), 3.08 (1H, dd, J=17.2, 12.8 Hz), 3.22 (2H, d, J=7.0 Hz), 5.06 (1H, t, J=7.0 Hz), 5.41 (1H, dd, J=12.8, 2.8 Hz), 6.25 (1H, s), 7.13 (2H, d, J=8.8 Hz), 7.44 (2H, d, J=8.8 Hz), 12.13 (1H, s); $^{13}$C-NMR (100 MHz CDCl$_3$) δ:13.90, 14.31, 20.95, 21.11, 21.17, 21.57, 32.33, 38.99, 43.75, 78.52, 102.06, 106.16, 115.39, 121.23, 122.05, 127.28, 135.74, 140.28, 150.88, 156.55, 159.59, 161.27, 168.38, 169.33, 197.03; IR (neat): 2959, 1768, 1752, 1647, 1628, 1587, 1507, 1431, 1373, 1219, 1194, 1163, 1142, 1086, 1065 cm$^{-1}$; mp: 72-74° C.

Acetic acid 4-[7-acetoxy-6-(2-cyclopentylidene-ethyl)-5-hydroxy-4-oxo-chroman-2-yl]-phenyl Ester (2c)

$^1$H-NMR (400 MHz CDCl$_3$) δ:1.57 (2H, quin, J=6.8 Hz), 1.67 (2H, quin, J=6.8 Hz), 2.18 (2H, t, J=6.8 Hz), 2.29 (3H, s), 2.30 (3H, s), 2.32 (2H, t, J=6.8 Hz), 2.83 (1H, dd, J=17.2, 3.2 Hz), 3.06 (1H, dd, J=17.2, 13.6 Hz), 3.18 (2H, d, J=6.8 Hz), 5.21 (1H, t, J=6.8 Hz), 5.40 (1H, dd, J=13.6, 3.2 Hz), 6.25 (1H, s), 7.13 (2H, d, J=8.4 Hz), 7.44 (2H, d, J=8.4 Hz), 12.15 (1H, s); $^{13}$C-NMR (100 MHz CDCl$_3$) δ:20.93, 21.10, 23.41, 26.33, 26.41, 28.68, 33.56, 43.70, 78.51, 102.02, 106.16, 115.16, 116.61, 122.03, 127.27, 135.71, 144.20, 150.85, 156.43, 159.54, 161.24, 168.40, 169.32, 197.02; IR (neat): 2962, 1769, 1751, 1653, 1646, 1636, 1586, 1559, 1507, 1436, 1369, 1198, 1137, 1087 cm$^{-1}$; mp: 67-69° C.

Under an Ar atmosphere, K$_2$CO$_3$ (0.60 mmol) was added to a solution of the obtained intermediate compounds (2a) to (2c)(0.20 mmol) in NeOH (2 mL) at room temperature, and the mixture was stirred at room temperature for 30 minutes. After completion of the reaction, 10% HCl (aq.) (1 mL) was added to the mixture, and it was extracted with EtOAc (3 mL×5) and dried over MgSO$_4$, and the solvent was distilled off.

The obtained residue was purified by silica gel column chromatography (hexane:EtOAc=1:1 (volume ratio))(Rf value=0.50 by thin-layer chromatography) to obtain yellow crystalline Compounds-40 to 41 and 48.

The physical properties of the obtained Compounds-40 to 41 and 48 were as follows.

6-(3-ethyl-pent-2-enyl)-5,7-dihydroxy-2-(4-hydroxy-phenyl)-chroman-4-one (Compound-40)

$^1$H-NMR (400 MHz Acetone-d6) δ:0.93 (3H, t, J=7.2 Hz), 1.01 (3H, t, J=7.2 Hz), 1.98 (2H, q, J=7.2 Hz), 2.23 (2H, q, J=7.2 Hz), 2.70 (1H, dd, J=17.2, 3.2 Hz), 3.16 (1H, dd, J=17.2, 12.8 Hz), 3.28 (2H, d, J=7.2 Hz), 5.19 (1H, t, J=7.2 Hz), 5.42 (1H, dd, J=12.8, 3.2 Hz), 6.02 (1H, s), 6.88 (2H, d, J=8.4 Hz), 7.38 (2H, d, J=8.4 Hz), 8.53 (1H, br), 9.46 (1H, br), 12.48 (1H, s); $^{13}$C-NMR (100 MHz Acetone-d6) δ:12.35, 12.72, 20.32, 22.85, 28.94, 42.08, 79.07, 94.51, 102.30, 108.30, 115.34, 120.77, 128.20, 130.11, 141.84, 157.85, 161.20, 161.49, 164.00, 196.56; IR (neat): 2965, 1653, 1646, 1635, 1616, 1587, 1558, 1521, 1517, 1507, 1490, 1457, 1447, 1337, 1309, 1297, 1170, 1153, 1085, 830 cm-1; mp: 208-210° C.

6-(2-cyclopentylidene-ethyl)-5,7-dihydroxy-2-(4-hydroxy-phenyl)-chroman-4-one (Compound-41)

$^1$H-NMR (400 MHz Acetone-d6) δ:1.55 (2H, quin, J=7.2 Hz), 1.65 (2H, quin, J=7.2 Hz), 2.15 (2H, t, J=7.2 Hz), 2.39 (2H, t, J=7.2 Hz), 2.70 (1H, dd, J=17.2, 2.8 Hz), 3.15 (1H, dd, J=17.2, 12.8 Hz), 3.22 (2H, d, J=7.2 Hz), 5.32 (1H, tt, J=7.2, 2.0 Hz), 5.40 (1H, dd, J=12.8, 2.8 Hz), 6.02 (1H, s), 6.88 (2H, d, J=8.4 Hz), 7.37 (2H, d, J=8.4 Hz), 9.03 (2H, br), 12.47 (1H, s); $^{13}$C-NMR (100 MHz Acetone-d6) δ:23.02, 26.94, 27.04, 29.04, 34.08, 43.55, 79.81, 95.25, 103.06, 108.95, 116.10, 118.85, 128.96, 130.88, 143.13, 158.58, 161.92, 162.22, 164.70, 197.28; IR (neat): 2969, 1653, 1646, 1635, 1616, 1586, 1559, 1521, 1517, 1507, 1497, 1490, 1472, 1457, 1448, 1437, 1339, 1310, 1296, 1245, 1220, 1160, 1085, 830 cm$^{-1}$; mp: 217-219° C.

5,7-dihydroxy-2-(4-hydroxy-phenyl)-6-(3-propyl-hex-2-enyl)-chroman-4-one (Compound-48)

$^1$H-NMR (400 MHz Acetone-d6) δ:0.82 (3H, t, J=7.4 Hz), 0.93 (3H, t, J=7.4 Hz), 1.31-1.49 (4, m), 1.92 (2H, t, J=7.4 Hz), 2.18 (2H, t, J=7.4 Hz), 2.69 (1H, dd, J=17.2, 2.8 Hz), 3.15 (1H, dd, J=17.2, 12.8 Hz), 3.28 (2H, d, J=7.6 Hz), 5.25 (1H, t, J=7.6 Hz), 5.40 (1H, dd, J=12.8, 2.8 Hz), 6.02 (1H, s), 6.88 (2H, d, J=8.4 Hz), 7.37 (2H, d, J=8.4 Hz), 12.48 (1H, br); $^{13}$C-NMR (100 MHz Acetone-d6) δ:14.11, 14.54, 21.29, 21.91, 22.33, 32.63, 39.72, 43.59, 79.83, 95.30, 103.35, 109.13, 116.11, 123.75, 128.97, 130.90, 139.29, 158.64, 161.88, 162.25, 164.77, 197.26; IR (neat): 2959, 1638, 1616, 1601, 1518, 1491, 1456, 1340, 1310, 1252, 1215, 1153, 1086, 833 cm$^{-1}$; mp: 130-132° C.

3$^1$, 10% Pd/C (3 mg) was added to a solution of Compounds-40 to 41 (0.15 mmol) in EtOAc (3 mL), and the mixture was stirred under a hydrogen atmosphere at room temperature for 20 hours. After completion of the reaction, the reaction solution was filtered through Celite, and the solvent was distilled off to obtain yellow crystalline Compounds-39 and 46 to 47.

The physical properties of the obtained Compounds-39 and 46 to 47 were as follows.

5,7-dihydroxy-2-(4-hydroxy-phenyl)-6-(3-methyl-butyl)-chroman-4-one (Compound-39)

$^1$H-NMR (400 MHz DMSO-d6) δ:0.88 (6H, d, J=6.4 Hz), 1.28 (2H, q, J=7.6 Hz), 1.42-1.54 (1H, m), 2.41 (1H, d, J=7.6 Hz), 2.43 (1H, d, J=7.6 Hz), 2.63 (1H, dd, J=17.2, 2.8 Hz), 3.22 (1H, dd, J=17.2, 12.8 Hz), 5.38 (1H, dd, J=12.8, 2.8 Hz), 5.93 (1H, s), 6.77 (2H, d, J=8.4 Hz), 7.29 (2H, d, J=8.4 Hz), 9.62 (1H, br), 12.41 (1H, s); $^{13}$C-NMR (100 MHz DMSO-d6) δ:19.47, 22.57, 27.59, 37.75, 42.12, 78.30, 94.41, 101.35, 108.59, 115.15, 128.31, 129.08, 157.70, 160.43, 160.74, 162.57, 196.28; IR (neat): 2951, 1632, 1587, 1519, 1489, 1453, 1382, 1337, 1310, 1296, 1248, 1210, 1185, 1158, 1129, 1085, 1055, 830 cm$^{-1}$; mp: 217-219° C.

6-(3-ethyl-pentyl)-5,7-dihydroxy-2-(4-hydroxy-phenyl)-chroman-4-one (Compound-46)

$^1$H-NMR (400 MHz Acetone-d6) δ:0.87 (6H, t, J=7.2 Hz), 1.20-1.27 (1H, m), 1.31-1.41 (4H, m), 1.43-1.49 (2H, m), 2.52 (1H, d, J=8.0 Hz), 2.54 (1H, d, J=8.0 Hz), 2.70 (1H, dd, J=17.2, 2.8 Hz), 3.16 (1H, dd, J=17.2, 12.8 Hz), 5.41 (1H, dd, J=12.8, 2.8 Hz), 6.01 (1H, s), 6.88 (2H, d, J=8.4 Hz), 7.38 (2H, d, J=8.4 Hz), 8.52 (1H, br), 9.55 (1H, br), 12.46 (1H, s); $^{13}$C-NMR (100 MHz Acetone-d6) 5:11.16, 19.64, 26.06, 32.31, 41.33, 43.61, 79.84, 95.20, 103.01, 110.20, 116.10, 128.70, 130.90, 158.62, 161.83, 162.38, 164.89, 197.31; IR (neat): 2960, 1635, 1587, 1518, 1489, 1458, 1338, 1308, 1296, 1261, 1244, 1186, 1161, 1105, 1084, 829 cm$^{-1}$; mp: 206-208° C.

6-(2-cyclopentyl-ethyl)-5,7-dihydroxy-2-(4-hydroxy-phenyl)-chroman-4-one (Compound-47)

$^1$H-NMR (400 MHz Acetone-d6) δ:1.09-1.21 (2H, m), 1.44-1.54 (4H, m), 1.54-1.63 (2H, m), 1.76-1.85 (3H, m), 2.56 (1H, d, J=8.0 Hz), 2.58 (1H, d, J=8.0 Hz), 2.70 (1H, dd, J=17.2, 2.8 Hz), 3.16 (1H, dd, J=17.2, 12.8 Hz), 5.41 (1H, dd, J=12.8, 2.8 Hz), 6.01 (1H, s), 6.88 (2H, d, J=8.4 Hz), 7.38 (2H, d, J=8.4 Hz), 8.51 (1H, s), 9.48 (1H, s), 12.45 (1H, s); $^{13}$C-NMR (100 MHz Acetone-d6) δ:21.69, 25.83, 33.28, 36.19, 40.90, 43.61, 79.84, 95.19, 103.01, 110.04, 116.10, 128.98, 130.90, 158.61, 161.84, 162.43, 164.88, 197.31; IR (neat): 2951, 1635, 1589, 1518, 1491, 1452, 1338, 1310, 1296, 1261, 1159, 1142, 1105, 1084, 829 cm$^{-1}$; mp: 224-226° C.

Synthesis of COMPOUNDS-33 TO 34, 36, 42 TO 43 AND 45

COMPOUND 33-34, 36, 42-43, 45

COMPOUND-43: R¹ = H, R² = Me, n = 1, 2-OH (84%)
COMPOUND-33: R¹ = OH, R² = Me, n = 1, 2-OH (87%)
COMPOUND-46: R¹ = OH, R² = Et, n = 1, 2-OH (80%)
COMPOUND-34: R¹ = OH, R² = Me, n = 1, 3-OH (73%)
COMPOUND-42: R¹ = OH, R² = Me, n = 2, 2,5-di-OH (97%)
COMPOUND-36: R¹ = OH, R² = Me, n = 2, 3,4-di-OH (80%)

Under an Ar atmosphere, aldehyde (3.60 mmol) and Ba(OH)$_2$ (4.32 mmol) were sequentially added to a solution of 1-(2-allyloxy-6-hydroxy-phenyl)-ethanone 4a² (1.20 mmol) or 1-(2-allyloxy-6-hydroxy-4-methoxymethoxy-phenyl)-ethanone 4b (1.20 mmol) in EtOH (5 mL) at room temperature, and the mixture was heated at 40° C. for 20 hours. After cooling, the mixture was filtered through Celite, and the solvent was distilled off. Then, H$_2$O (5 mL) and 10% HCl (aq.) (1 mL) were added to the reactant, it was extracted with EtOAc (3 mL×3), dried over MgSO$_4$, and the solvent was distilled off. The obtained residue was purified by silica gel column chromatography (hexane:EtOAc=10:1 (volume ratio))(Rf value=0.20 by thin-layer chromatography) to obtain yellow oily substances 5a, 5c to 5d, and yellow crystals 5b and 5e The physical properties of the obtained intermediate compounds 5a to 5e were as follows.

1-(2-allyloxy-6-hydroxy-phenyl)-3-(2-methoxymethoxy-phenyl)-propenone (5a)

$^1$H-NMR (400 MHz CDCl$_3$) δ:3.51 (3H, s), 4.66 (2H, dt, J=6.8, 2.0 Hz), 5.28 (2H, s), 5.32 (1H, dd, J=11.2, 2.0 Hz), 5.46 (1H, dd, J=17.2, 2.0 Hz), 6.12 (1H, ddt, J=17.2, 11.2, 6.8 Hz), 6.42 (1H, d, J=8.0 Hz), 6.62 (1H, d, J=8.0 Hz), 7.02 (1H, t, J=8.0 Hz), 7.18 (1H, d, J=8.0 Hz), 7.34 (2H, t, J=8.0 Hz), 7.65 (1H, dd, J=8.0, 2.0 Hz), 7.94 (1H, d, J=15.6 Hz), 8.26 (1H, d, J=15.6 Hz), 13.10 (1H, s); $^{13}$C-NMR (100 MHz CDCl$_3$) δ:56.26, 69.71, 94.56, 102.61, 110.97, 111.96, 114.88, 118.51, 121.78, 124.85, 127.73, 127.81, 131.61, 132.36, 135.65, 137.59, 156.38, 159.85, 164.66, 194.70; IR (neat): 1629, 1598, 1577, 1570, 1558, 1485, 1472, 1457, 1448, 1355, 1235, 1200, 1153, 1078, 1028, 990, 754 cm$^{-1}$.

1-(2-allyloxy-6-hydroxy-4-methoxymethoxy-phenyl)-3-(2-methoxymethoxy-phenyl)-propenone (5b)

$^1$H-NMR (400 MHz CDCl$_3$) δ:3.49 (3H, s), 3.51 (3H, s), 4.62 (2H, d, J=5.2 Hz), 5.20 (2H, s), 5.27 (2H, s), 5.34 (1H, d, J=10.8 Hz), 5.47 (1H, d, J=17.2 Hz), 6.07 (1H, d, J=2.4 Hz), 6.11 (1H, ddt, J=17.2, 10.8, 5.2 Hz), 6.27 (1H, d, J=2.4 Hz), 7.01 (1H, t, J=7.6 Hz), 7.18 (1H, d, J=7.6 Hz), 7.33 (1H, td, J=7.6, 1.6 Hz), 7.64 (1H, dd, J=7.6, 1.6 Hz), 7.96 (1H, d, J=15.6 Hz), 8.23 (1H, d, J=15.6 Hz), 14.03 (1H, s); $^{13}$C-NMR (100 MHz CDCl$_3$) 5:56.21, 56.37, 69.72, 92.65, 93.97, 94.52, 96.65, 107.22, 114.83, 118.83, 121.74, 125.02, 127.58, 127.69, 131.37, 132.14, 137.02, 156.22, 161.41, 163.41, 167.51, 193.09; IR (neat): 1622, 1576, 1558, 1343, 1235, 1217, 1204, 1161, 1153, 1104, 1076, 1040, 991, 950, 835 cm$^{-1}$; mp: 94-96° C.

1-(2-allyloxy-6-hydroxy-4-methoxymethoxy-phenyl)-3-(3-methoxymethoxy-phenyl)-propenone (5c)

$^1$H-NMR (400 MHz CDCl$_3$) δ:3.43 (3H, s), 3.45 (3H, s), 4.56 (2H, d, J=5.6 Hz), 5.15 (2H, s), 5.16 (2H, s), 5.30 (1H, d, J=10.4 Hz), 5.42 (1H, d, J=17.2 Hz), 6.02 (1H, d, J=2.4 Hz), 6.10 (1H, ddt, J=17.2, 10.4, 5.6 Hz), 6.22 (1H, d, J=2.4 Hz), 7.07 (1H, d, J=8.0 Hz), 7.23 (3H, m), 7.66 (1H, d, J=15.6 Hz), 7.89 (1H, d, J=15.6 Hz), 13.92 (1H, s); $^{13}$C-NMR (100 MHz CDCl$_3$) δ:55.98, 56.39, 69.80, 92.61, 93.98, 94.32, 96.65, 107.10, 115.53, 118.06, 119.09, 122.36, 127.91, 129.75, 132.06, 136.82, 142.02, 157.54, 161.45, 163.57, 167.61, 192.77; IR (neat): 1653, 1634, 1623, 1617, 1577, 1569, 1558, 1505, 1343, 1218, 1151, 1082, 1025 cm$^{-1}$.

1-(2-allyloxy-6-hydroxy-4-methoxymethoxy-phenyl)-3-(2,6-bis-methoxymethoxy-phenyl)-propenone (5d)

$^1$H-NMR (400 MHz CDCl$_3$) δ:3.48 (6H, s), 3.49 (3H, s), 4.65 (2H, d, J=4.8 Hz), 5.20 (1H, dd, J=10.4, 1.2 Hz), 5.25 (6H, s), 5.39 (1H, dd, J=17.2, 1.2 Hz), 6.02 (1H, ddt, J=17.2, 10.4, 4.8 Hz), 6.06 (1H, d, J=2.4 Hz), 6.27 (1H, d, J=2.4 Hz), 6.85 (2H, d, J=8.0 Hz), 7.23 (1H, t, J=8.0 Hz), 8.26 (2H, d, J=10.4 Hz), 14.02 (1H, s); $^{13}$C-NMR (100 MHz CDCl$_3$) δ:56.27, 56.38, 69.68, 92.95, 94.01, 94.64, 96.66, 107.68, 108.12, 115.0, 117.61, 131.03, 132.41, 133.54, 157.74, 161.45, 163.16, 167.25, 194.48; IR (neat: 1623, 1595, 1577, 1573, 1558, 1472, 1334, 1202, 1152, 1100, 1083, 1037, 921 cm$^{-1}$.

1-(2-allyloxy-6-hydroxy-4-methoxymethoxy-phenyl)-3-(3,4-bis-methoxymethoxy-phenyl)-propenone (5e)

$^1$H-NMR (400 MHz CDCl$_3$) δ:3.47 (3H, s), 3.51 (3H, s), 3.52 (3H, s), 4.60 (2H, d, J=5.6 Hz), 5.18 (2H, s), 5.25 (2H, s), 5.26 (2H, s), 5.33 (1H, dd, J=10.4, 1.2 Hz), 5.46 (1H, dd, J=17.2, 1.2 Hz), 6.05 (1H, d, J=2.4 Hz), 6.15 (1H, ddt, J=17.2, 10.4, 5.6 Hz), 6.25 (1H, d, J=2.4 Hz), 7.15 (1H, d, J=8.4 Hz), 7.20 (1H, d, J=8.4 Hz), 7.42 (1H, d, J=1.6 Hz), 7.72 (1H, d, J=16.4 Hz), 7.85 (1H, d, J=16.4 Hz), 14.05 (1H, s); $^{13}$C-NMR (100 MHz CDCl$_3$) δ: 56.22, 56.29, 56.37, 69.80, 92.57, 93.98, 95.03, 95.36, 96.65, 107.11, 115.61, 115.97, 118.93, 124.02, 126.04, 129.84, 132.13, 142.31, 147.27, 149.06, 161.38, 163.39, 167.58, 192.66; IR (neat): 1652, 1628, 1598, 1577, 1558, 1507, 1419, 1345, 1257, 1221, 1199, 1155, 1131, 1104, 1092, 1079, 1026, 1009, 997, 978 cm$^{-1}$; mp: 63-64° C.

NaOAc (3.60 mmol) was added to a solution of (5a) to (5e)(0.60 mmol) in EtOH/H$_2$O (9:1, 5 mL) at room temperature, and the mixture was heated under reflux for 24 hours. After cooling, the solvent was distilled off, then extracted with CH$_2$Cl$_2$ (3 mL×3), dried over MgSO$_4$, and the solvent was distilled off. The obtained residue was purified by silica gel column chromatography (hexane:EtOAc=3:1 (volume ratio)) (Rf value=0.30 by thin-layer chromatography), and yellow oily substances 6a, 6c, yellow crystals 6b, 6d to 6e.

The physical properties of the obtained intermediate compounds (6a) to (6e) were as follows.

5-allyloxy-2-(2-methoxymethoxy-phenyl)-chroman-4-one (6a)

$^1$H-NMR (400 MHz CDCl$_3$) δ:2.91 (2H, d, J=7.6 Hz), 3.34 (3H, s), 4.63 (2H, d, J=4.0 Hz), 5.18 (2H, s), 5.32 (1H, d, J=10.8 Hz), 5.66 (1H, d, J=17.2 Hz), 5.80 (1H, t, J=7.6 Hz), 6.07 (1H, ddt, J=17.2, 10.8, 4.0 Hz), 6.51 (1H, d, J=8.4 Hz), 6.65 (1H, d, J=8.4 Hz), 7.07 (1H, t, J=7.6 Hz), 7.12 (1H, d, J=7.6 Hz), 7.28 (1H, t, J=7.6 Hz), 7.35 (1H, t, J=8.4 Hz), 7.60 (1H, d, J=7.6 Hz); $^{13}$C-NMR (100 MHz CDCl$_3$) δ:45.31, 56.20, 69.36, 74.12, 94.24, 105.18, 110.26, 111.89, 113.79, 117.48, 121.97, 126.35, 128.00, 129.31, 132.32, 135.70, 153.45, 159.68, 163.62, 191.04; IR (neat): 1694, 1684, 1602, 1575, 1558, 1507, 1490, 1472, 1457, 1259, 1153, 1078, 992 cm$^{-1}$.

5-allyloxy-7-methoxymethoxy-2-(2-methoxymethoxy-phenyl)-chroman-4-one (6b)

$^1$H-NMR (400 MHz CDCl$_3$) δ:2.67 (2H, d, J=7.2 Hz), 3.45 (3H, s), 3.48 (3H, s), 4.62 (2H, dd, J=4.8, 1.6 Hz), 5.18 (2H, s), 5.19 (2H, s), 5.35 (1H, dd, J=10.8, 1.6 Hz), 5.69 (1H, dd, J=17.2, 1.6 Hz), 5.80 (1H, t, J=7.2 Hz), 6.09 (1H, ddt, J=17.2, 10.8, 4.8 Hz), 6.20 (1H, d, J=2.4 Hz), 6.45 (1H, d, J=2.4 Hz), 7.09 (1H, t, J=8.0 Hz), 7.13 (1H, d, J=8.0 Hz), 7.30 (1H, td, J=8.0, 2.0 Hz), 7.61 (1H, dd, J=8.0, 2.0 Hz); $^{13}$C-NMR (100 MHz CDCl$_3$) δ:45.00, 56.18, 56.36, 69.30, 74.26, 94.01, 94.18, 94.97, 96.23, 106.83, 113.07, 117.55, 121.91, 126.27, 128.00, 129.22, 132.09, 153.38, 161.13, 163.19, 165.05, 189.74; IR (neat): 1683, 1669, 1608, 1576, 1559, 1490, 1458, 1437, 1355, 1257, 1251, 1233, 1215, 1153, 1126, 1111, 1053, 1046, 1035, 998, 993, 950, 925, 917, 826, 754 cm$^{-1}$; mp: 80-82° C.

5-allyloxy-7-methoxymethoxy-2-(3-methoxymethoxy-phenyl)-chroman-4-one (6c)

$^1$H-NMR (400 MHz CDCl$_3$) δ:2.79 (1H, dd, J=17.2, 2.4 Hz), 3.00 (1H, dd, J=17.2, 12.8 Hz), 3.48 (3H, s), 3.49 (3H, s), 4.61 (2H, d, J=4.8 Hz), 5.17 (2H, d, J=1.2 Hz), 5.20 (2H, d, J=1.2 Hz), 5.34 (1H, dd, J=10.4, 1.6 Hz), 5.37 (1H, dd, J=12.8, 2.4 Hz), 5.66 (1H, dd, J=17.2, 1.6 Hz), 6.07 (1H, ddt, J=17.2, 10.4, 4.8 Hz), 6.19 (1H, d, J=2.4 Hz), 6.34 (1H, d, J=2.4 Hz), 7.04 (1H, dd, J=8.0, 2.0 Hz), 7.08 (1H, d, J=8.0 Hz), 7.13 (1H, t, J=2.0 Hz), 7.33 (1H, t, J=8.0 Hz); $^{13}$C-NMR (100 MHz CDCl$_3$) δ:45.65, 55.96, 56.33, 69.32, 78.84, 93.99, 94.31, 95.09, 96.21, 106.70, 114.01, 116.11, 117.60, 119.34, 129.77, 132.06, 140.30, 157.46, 161.01, 163.25, 164.46, 188.90; IR (neat): 1683, 1680, 1608, 1573, 1436, 1259, 1211, 1150, 1124, 1107, 1083, 1055, 1031, 994 cm$^{-1}$.

5-allyloxy-2-(2,6-bis-methoxymethoxy-phenyl)-7-methoxymethoxy-chroman-4-one (6d)

$^1$H-NMR (400 MHz CDCl$_3$) δ:2.54 (1H, dd, J=17.2, 3.2 Hz), 3.44 (6H, s), 3.45 (3H, s), 3.82 (1H, dd, J=17.2, 14.0 Hz), 4.62 (2H, d, J=6.4 Hz), 5.14 (2H, d, J=3.2 Hz), 5.17 (4H, s), 5.33 (1H, dd, J=10.4, 1.2 Hz), 5.68 (1H, dd, J=17.2, 1.2 Hz), 6.08 (1H, ddt, J=17.2, 10.4, 6.4 Hz), 6.09 (1H, dd, J=14.0, 3.2 Hz), 6.17 (1H, d, J=2.4 Hz), 6.23 (1H, d, J=2.4 Hz), 6.82 (2H, d, J=8.4 Hz), 7.23 (1H, t, J=8.4 Hz); $^{13}$C-NMR (100 MHz CDCl$_3$) δ:42.12, 56.25, 56.34, 69.32, 71.66, 93.99, 94.55, 96.01, 106.80, 108.56, 115.63, 117.54, 130.41, 132.22, 156.56, 161.23, 162.96, 165.66, 190.86; IR (neat): 1683, 1669, 1616, 1601, 1576, 1472, 1265, 1246, 1153, 1107, 1098, 1087, 1047, 1035, 919 cm$^{-1}$; mp: 79-81° C.

5-allyloxy-2-(3,4-bis-methoxymethoxy-phenyl)-7-methoxymethoxy-chroman-4-one (6e)

$^1$H-NMR (400 MHz CDCl$_3$) δ:2.77 (1H, dd, J=17.2, 3.2 Hz), 3.07 (1H, dd, J=17.2, 13.6 Hz), 3.33 (2H, d, J=6.0 Hz), 3.43 (3H, s), 3.50 (3H, s), 3.51 (3H, s), 4.94 (1H, dd, J=10.4, 2.0 Hz), 4.99 (1H, dd, J=17.2, 2.0 Hz), 5.18 (2H, d, J=3.2 Hz), 5.23 (2H, s), 5.24 (2H, d, J=3.2 Hz), 5.32 (1H, dd, J=13.6, 3.2 Hz), 5.92 (1H, ddt, J=17.2, 10.4, 6.0 Hz), 6.27 (1H, s), 7.02 (1H, dd, J=8.4, 2.0 Hz), 7.18 (1H, d, J=8.4 Hz), 7.24 (1H, d, J=2.0 Hz), 12.10 (1H, s); $^{13}$C-NMR (100 MHz CDCl$_3$) δ:26.16, 43.36, 56.17, 56.25, 56.36, 78.93, 93.42, 93.74, 95.26, 95.44, 103.34, 108.74, 114.23, 114.73, 116.57, 120.30, 132.52, 136.07, 147.40, 147.53, 160.68, 161.21, 162.87, 196.17; IR (neat): 1653, 1636, 1577, 1559, 1521, 1516, 1507, 1433, 1261, 1157, 1130, 1091, 1076, 1057, 993, 962, 923 cm$^{-1}$; mp: 79-80 $^1$H-NMR (400 MHz CDCl$_3$) δ:2.92 (1H, d, J=4.4 Hz), 2.94 (1H, d, J=12.4 Hz), 3.36 (2H, d, J=6.0 Hz), 3.46 (3H, s), 3.47 (3H, s), 4.97 (1H, dd, J=10.0, 1.6 Hz), 5.02 (1H, dd, J=17.2, 1.6 Hz), 5.22 (4H, s), 5.78 (1H, dd, J=12.4, 4.4 Hz), 5.95 (1H, ddt, J=17.2, 10.0, 6.0 Hz), 6.32 (1H, s), 7.10 (1H, t, J=8.0 Hz), 7.15 (1H, d, J=8.0 Hz), 7.32 (1H, t, J=8.0 Hz), 7.61 (1H, d, J=8.0 Hz), 12.19 (1H, s); $^{13}$C-NMR (100 MHz CDCl$_3$) δ:26.18, 42.72, 56.20, 56.37, 74.36, 93.38, 93.76, 94.25, 103.40, 108.63, 113.83, 114.24, 122.02, 126.41, 127.67, 129.45, 136.10, 153.42, 160.77, 161.69, 162.79, 196.86; IR (neat): 1644, 1578, 1506, 1497, 1448, 1437, 1311, 1292, 1285, 1240, 1223, 1155, 1128, 1083, 1049, 997, 960, 913, 763 cm$^{-1}$; mp: 114-115° C.

Under an Ar atmosphere, Eu (fod)$_3$ (0.043 mmol) was added to a solution of (6a) to (6e) (0.43 mmol) in ClCH$_2$CH$_2$Cl (5 mL) at room temperature, and the mixture was heated at 100° C. in a sealed tube for 20 hours. After cooling, the solvent was distilled off, and the obtained residue was purified by silica gel column chromatography (hexane:EtOAc=10:1 (volume ratio)) (Rf value=0.35 by thin-layer chromatography) to give a yellow oil. Substance 7a and yellow crystals 7b to 7e were obtained.

The physical properties of the obtained intermediate Compounds (7a) to (7e) were as follows.

6-allyl-5-hydroxy-2-(2-methoxymethoxy-phenyl)-chroman-4-one (7a)

$^1$H-NMR (400 MHz CDCl$_3$) δ:2.96 (1H, d, J=4.8 Hz), 2.98 (1H, d, J=12.4 Hz), 3.33 (2H, d, J=6.0 Hz), 3.45 (3H, s), 5.05 (1H, dd, J=10.0, 1.6 Hz), 5.07 (1H, dd, J=17.2, 1.6 Hz), 5.20 (2H, d, J=3.2 Hz), 5.80 (1H, dd, J=12.4, 4.8 Hz), 5.96 (1H, ddt, J=17.2, 10.0, 6.0 Hz), 6.47 (1H, d, J=8.4 Hz), 7.09 (1H, t, J=7.2 Hz), 7.14 (1H, d, J=7.2 Hz), 7.26 (1H, d, J=8.4 Hz), 7.31 (1H, td, J=7.2, 1.2 Hz), 7.61 (1H, dd, J=7.2, 1.2 Hz), 12.03 (1H, s); $^{13}$C-NMR (100 MHz CDCl$_3$) δ:32.61, 43.12, 56.23, 74.23, 94.30, 106.95, 107.81, 113.92, 115.56, 120.09, 122.07, 126.47, 127.66, 129.54, 136.36, 138.55, 153.49, 159.50, 160.28, 198.88; IR (neat): 1651, 1644, 1639, 1634, 1494, 1455, 1442, 1435, 1362, 1234, 1154, 1080, 1061, 995, 755 cm$^{-1}$.

6-allyl-5-hydroxy-7-methoxymethoxy-2-(2-methoxymethoxy-phenyl)-chroman-4-one (7b)

$^1$H-NMR (400 MHz CDCl$_3$) δ:2.92 (1H, d, J=4.4 Hz), 2.94 (1H, d, J=12.4 Hz), 3.36 (2H, d, J=6.0 Hz), 3.46 (3H, s), 3.47 (3H, s), 4.97 (1H, dd, J=10.0, 1.6 Hz), 5.02 (1H, dd, J=17.2, 1.6 Hz), 5.22 (4H, s), 5.78 (1H, dd, J=12.4, 4.4 Hz), 5.95 (1H, ddt, J=17.2, 10.0, 6.0 Hz), 6.32 (1H, s), 7.10 (1H, t, J=8.0 Hz), 7.15 (1H, d, J=8.0 Hz), 7.32 (1H, t, J=8.0 Hz), 7.61 (1H, d, J=8.0 Hz), 12.19 (1H, s); $^{13}$C-NMR (100 MHz CDCl$_3$) δ:26.18, 42.72, 56.20, 56.37, 74.36, 93.38, 93.76, 94.25, 103.40, 108.63, 113.83, 114.24, 122.02, 126.41, 127.67, 129.45, 136.10, 153.42, 160.77, 161.69, 162.79, 196.86; IR (neat): 1644, 1578, 1506, 1497, 1448, 1437, 1311, 1292, 1285, 1240, 1223, 1155, 1128, 1083, 1049, 997, 960, 913, 763 cm$^{-1}$; mp: 114-115° C.

6-allyl-5-hydroxy-7-methoxymethoxy-2-(3-methoxymethoxy-phenyl)-chroman-4-one (7c)

$^1$H-NMR (400 MHz CDCl$_3$) δ:2.91 (1H, dd, J=17.2, 2.4 Hz), 3.16 (1H, dd, J=17.2, 13.6 Hz), 3.37 (2H, d, J=6.4 Hz), 3.47 (3H, s), 3.49 (3H, s), 4.97 (1H, dd, J=10.4, 1.2 Hz), 5.03 (1H, dd, J=17.2, 1.2 Hz), 5.21 (2H, d, J=1.2 Hz), 5.22 (2H, d, J=2.4 Hz), 5.42 (1H, dd, J=13.6, 2.4 Hz), 5.95 (1H, ddt, J=17.2, 10.4, 6.4 Hz), 6.33 (1H, s), 7.06 (1H, dd, J=8.0, 2.0 Hz), 7.09 (1H, d, J=8.0 Hz), 7.15 (1H, s), 7.34 (1H, t, J=8.0 Hz), 12.31 (1H, s); $^{13}$C-NMR (100 MHz CDCl$_3$) δ:26.23, 43.85, 56.05, 56.40, 79.15, 93.49, 93.81, 94.39, 103.22, 108.88, 114.08, 114.30, 116.40, 119.41, 129.93, 136.08, 140.01, 157.58, 160.93, 161.31, 163.04, 196.67; IR (neat): 1635, 1576, 1558, 1486, 1440, 1297, 1287, 1221, 1155, 1127, 1093, 1078, 1055, 1033, 966, 926 cm$^{-1}$; mp: 79-81° C.

6-allyl-2-(2,6-bis-methoxymethoxy-phenyl)-5-hydroxy-7-methoxymethoxy-chroman-4-one (7d)

$^1$H-NMR (400 MHz CDCl$_3$) δ:2.59 (1H, dd, J=17.2, 3.2 Hz), 3.36 (2H, d, J=6.4 Hz), 3.45 (3H, s), 3.48 (6H, s), 3.92 (1H, dd, J=17.2, 14.0 Hz), 4.97 (1H, d, J=10.0 Hz), 5.04 (1H, dd, J=17.2, 1.2 Hz), 5.20 (6H, s), 5.95 (1H, ddt, J=17.2, 10.0, 6.4 Hz), 6.10 (1H, dd, J=14.0, 3.2 Hz), 6.21 (1H, s), 6.85 (2H, d, J=8.4 Hz), 7.26 (1H, t, J=8.4 Hz), 12.32 (1H, s); $^{13}$C-NMR (100 MHz CDCl$_3$) δ:26.22, 39.90, 56.34, 56.40, 71.63, 93.08, 93.77, 94.66, 108.20, 108.62, 114.26, 115.26, 130.71, 136.28, 156.66, 160.88, 162.40, 162.63, 197.99; IR (neat): 1653, 1635, 1601, 1577, 1558, 1506, 1472, 1447, 1153, 1124, 1099, 1082, 1048 cm$^{-1}$; mp: 87-89° C.

6-allyl-2-(3,4-bis-methoxymethoxy-phenyl)-5-hydroxy-7-methoxymethoxy-chroman-4-one (7e)

$^1$H-NMR (400 MHz CDCl$_3$) δ:2.77 (1H, dd, J=17.2, 3.2 Hz), 3.07 (1H, dd, J=17.2, 13.6 Hz), 3.33 (2H, d, J=6.0 Hz), 3.43 (3H, s), 3.50 (3H, s), 3.51 (3H, s), 4.94 (1H, dd, J=10.4, 1.2 Hz), 4.99 (1H, dd, J=17.2, 1.2 Hz), 5.18 (2H, d, J=3.2 Hz), 5.23 (2H, s), 5.24 (2H, d, J=3.2 Hz), 5.32 (1H, dd, J=13.6, 3.2 Hz), 5.92 (1H, ddt, J=17.2, 10.4, 6.0 Hz), 6.27 (1H, s), 7.02 (1H, dd, J=8.4, 2.0 Hz), 7.18 (1H, d, J=8.4 Hz), 7.24 (1H, d, J=2.0 Hz), 12.10 (1H, s); $^{13}$C-NMR (100 MHz CDCl$_3$) δ:26.16, 43.36, 56.17, 56.25, 56.36, 78.93, 93.42, 93.74, 95.26, 95.44, 103.34, 108.74, 114.23, 114.73, 116.57, 120.30, 132.52, 136.07, 147.40, 147.53, 160.68, 161.21, 162.87, 196.17; IR (neat): 1653, 1636, 1577, 1559, 1521, 1516, 1507, 1433, 1261, 1157, 1130, 1091, 1076, 1057, 993, 962, 923 cm$^{-1}$; mp: 79-80° C.

HCl (3 drops) was added to a solution of (7a) to (7e) (0.33 mmol) in MeOH (3 mL) at room temperature, and the mixture was stirred at room temperature for 3 days. After completion of the reaction, the solvent was distilled off, and the obtained residue was purified by silica gel column chromatography (CH$_2$Cl$_2$:MeOH=50:1 (volume ratio)) (Rf value=0.35 by thin-layer chromatography) to obtain yellow crystals (8a) to (8e).

The physical properties of the obtained intermediate Compounds (8a) to (8e) were as follows.

6-allyl-5-hydroxy-2-(2-hydroxyl-phenyl)-chroman-4-one (8a)

$^1$H-NMR (400 MHz Acetone-d6) δ:2.93 (1H, dd, J=17.2, 2.4 Hz), 3.19 (1H, dd, J=17.2, 13.6 Hz), 3.30 (2H, d, J=5.2 Hz), 5.00 (1H, d, J=10.4 Hz), 5.06 (1H, d, J=17.2 Hz), 5.84 (1H, dd, J=13.6, 2.4 Hz), 5.95 (1H, ddt, J=17.2, 10.4, 5.2 Hz), 6.49 (1H, d, J=8.0 Hz), 6.93 (1H, t, J=8.0 Hz), 6.94 (1H, d, J=8.0 Hz), 7.21 (1H, t, J=8.0 Hz), 7.32 (1H, d, J=8.0 Hz), 7.54 (1H, d, J=8.0 Hz), 8.77 (1H, s), 12.15 (1H, s); $^{13}$C-NMR (100 MHz Acetone-d6) δ:33.11, 43.02, 75.36, 107.73, 108.47, 115.81, 116.27, 120.42, 120.69, 126.23, 127.63, 130.20, 137.39, 139.18, 154.72, 160.18, 161.37, 200.18; IR (neat): 1625, 1609, 1490, 1462, 1437, 1348, 1234, 755, 736 cm$^{-1}$; mp: 184-186° C.

6-allyl-5,7-dihydroxy-2-(2-hydroxyl-phenyl)-chroman-4-one (8b)

$^1$H-NMR (400 MHz Acetone-d6) δ:2.82 (1H, dd, J=17.2, 3.2 Hz), 3.10 (1H, dd, J=17.2, 13.2 Hz), 3.30 (2H, d, J=6.4 Hz), 4.90 (1H, dd, J=10.4, 2.0 Hz), 5.00 (1H, dd, J=17.2, 2.0 Hz), 5.78 (1H, dd, J=13.2, 3.2 Hz), 5.91 (1H, ddt, J=17.2, 10.4, 6.4 Hz), 6.09 (1H, s), 6.93 (1H, d, J=8.0 Hz), 6.93 (1H, t, J=8.0 Hz), 7.21 (1H, td, J=8.0, 2.0 Hz), 7.52 (1H, dd, J=8.0, 2.0 Hz), 8.78 (1H, s), 9.62 (1H, s), 12.15 (1H, s); $^{13}$C-NMR (100 MHz Acetone-d6) δ:26.66, 42.50, 75.26, 95.25, 102.97, 107.21, 114.51, 116.21, 120.62, 126.34, 127.62, 130.10, 136.98, 154.70, 162.43, 164.77, 197.39; IR (neat): 1653, 1646, 1635, 1616, 1591, 1558, 1506, 1497, 1490, 1472, 1457, 1340, 1312, 1300, 1218, 1158, 1118, 826 cm$^{-1}$; mp: 174-176° C.

6-allyl-5,7-dihydroxy-2-(3-hydroxyl-phenyl)-chroman-4-one (8c)

$^1$H-NMR (400 MHz Acetone-d6) δ:2.78 (1H, dd, J=17.2, 3.2 Hz), 3.11 (1H, dd, J=17.2, 12.8 Hz), 3.29 (2H, d, J=6.0 Hz), 4.89 (1H, dd, J=10.4, 1.6 Hz), 4.99 (1H, dd, J=17.2, 1.6 Hz), 5.47 (1H, dd, J=12.8, 3.2 Hz), 5.90 (1H, ddt, J=17.2, 10.4, 6.0 Hz), 6.07 (1H, s), 6.84 (1H, dd, J=8.0, 2.4 Hz), 6.99 (1H, d, J=8.0 Hz), 7.02 (1H, d, J=2.4 Hz), 7.25 (1H, t, J=8.0 Hz), 8.55 (1H, br), 9.66 (1H, br), 12.44 (1H, s); $^{13}$C-NMR (100 MHz Acetone-d6) δ:26.66, 43.65, 79.74, 95.27, 103.02, 107.29, 114.09, 114.53, 116.22, 118.19, 130.52, 136.97, 141.59, 158.44, 161.99, 162.39, 164.88, 196.95; IR (neat): 1635, 1593, 1558, 1506, 1490, 1472, 1456, 1339, 1303, 1280, 1215, 1154, 1120, 1078 cm$^{-1}$; mp: 168-170° C.

6-allyl-2-(2,6-hydroxyl-phenyl)-5,7-dihydroxy-chroman-4-one (8d)

$^1$H-NMR (400 MHz Acetone-d6) δ:2.51 (1H, dd, J=17.2, 2.4 Hz), 3.28 (2H, d, J=6.0 Hz), 3.89 (1H, dd, J=17.2, 13.6 Hz), 4.87 (1H, d, J=10.0 Hz), 4.98 (1H, d, J=17.2 Hz), 5.89 (1H, ddt, J=17.2, 10.0, 6.0 Hz), 6.00 (1H, s), 6.02 (1H, dd, J=13.6, 2.4 Hz), 6.44 (2H, d, J=8.4 Hz), 7.00 (1H, t, J=8.4 Hz), 8.55 (2H, s), 9.56 (1H, s), 12.57 (1H, s); $^{13}$C-NMR (100 MHz Acetone-d6) δ:26.20, 39.74, 72.64, 94.46, 102.25, 106.29, 107.67, 110.95, 113.71, 130.17, 136.33, 156.99, 161.84, 162.17, 163.86, 197.69; IR (neat): 1653, 1635, 1601, 1558, 1506, 1472, 1456, 1451, 1447, 1312 cm$^{-1}$; mp: 214-216° C.

6-allyl-2-(3,4-hydroxyl-phenyl)-5,7-dihydroxy-chroman-4-one (8e)

$^1$H-NMR (400 MHz Acetone-d6) δ:2.7 (1H, dd, J=17.2, 3.2 Hz), 3.13 (1H, dd, J=17.2, 12.8 Hz), 3.28 (2H, dt, J=6.0, 2.0 Hz), 4.88 (1H, dd, J=10.0, 2.0 Hz), 4.98 (1H, dd, J=17.2, 2.0 Hz), 5.36 (1H, dd, J=12.8, 3.2 Hz), 5.90 (1H, ddt, J=17.2, 10.0, 6.0 Hz), 6.03 (1H, s), 6.86 (2H, s), 7.02 (1H, s), 8.08 (2H, br), 9.62 (1H, br), 12.46 (1H, s); $^{13}$C-NMR (100 MHz Acetone-d6) δ:26.64, 43.57, 79.87, 95.19, 102.95, 107.09, 114.49, 114.63, 115.92, 119.15, 131.53, 137.00, 145.90, 146.27, 162.18, 162.34, 164.86, 197.30; IR (neat): 1654, 1646, 1635, 1617, 1589, 1523, 1507, 1490, 1457, 1339, 1326, 1303, 1290, 1158, 1109 cm$^{-1}$; mp: 165-167° C.

Under an Ar atmosphere, a required amount of Ac2O was added to a solution of 8a to 8e (0.73 mmol) in pyridine (5 mL) at room temperature, and the mixture was stirred at room temperature for 14 hours. After completion of the reaction, the solvent was distilled off, and the obtained residue was purified by silica gel column chromatography (hexane:EtOAc=40:1 (volume ratio)) (Rf value=0.40 by thin-layer chromatography) to obtain yellow crystals (9a) to (9e).

The physical properties of the obtained intermediate Compounds (9a) to (9e) were as follows.

Acetic acid 2-(6-allyl-5-hydroxy-4-oxo-chroman-2-yl)-phenyl ester (9a)

$^1$H-NMR (400 MHz CDCl$_3$) δ:2.27 (3H, s), 2.83 (1H, dd, J=17.2, 2.4 Hz), 3.10 (1H, dd, J=17.2, 13.6 Hz), 3.32 (2H, d, J=6.4 Hz), 5.05 (1H, dd, J=10.4, 1.8 Hz), 5.06 (1H, dd, J=17.2, 1.8 Hz), 5.53 (1H, dd, J=13.6, 2.4 Hz), 5.95 (1H, ddt, J=17.2, 10.4, 6.4 Hz), 6.44 (1H, d, J=8.0 Hz), 7.13 (1H, dd, J=8.0, 1.2 Hz), 7.25 (1H, d, J=8.0 Hz), 7.32 (1H, td, J=8.0, 1.2 Hz), 7.40 (1H, td, J=8.0, 1.6 Hz), 7.62 (1H, dd, J=8.0, 1.6 Hz), 11.96 (1H, s); $^{13}$C-NMR (100 MHz CDCl$_3$) δ:20.92, 32.59, 42.82, 74.32, 106.91, 107.66, 115.75, 120.49, 123.00, 126.55, 127.19, 129.76, 130.33, 136.22, 138.73, 147.72, 159.47, 159.72, 169.06, 198.02; IR (neat): 1762, 1653, 1647, 1627, 1493, 1480, 1431, 1369, 1356, 1340, 1226, 1202, 1186, 1175, 1166, 1060, 919, 815 cm$^{-1}$; mp: 83-85° C.

Acetic acid 2-(2-acetoxy-phenyl)-6-allyl-5-hydroxy-4-oxo-chroman-7-yl ester (9b)

$^1$H-NMR (400 MHz CDCl$_3$) δ:2.30 (3H, s), 2.31 (3H, s), 2.84 (1H, dd, J=17.2, 3.2 Hz), 3.11 (1H, dd, J=17.2, 13.6 Hz), 3.28 (2H, dd, J=6.0, 1.2 Hz), 4.99 (1H, dd, J=10.4, 1.2 Hz), 5.03 (1H, dd, J=17.2, 1.2 Hz), 5.57 (1H, dd, J=13.6, 3.2 Hz), 5.85 (1H, ddt, J=17.2, 10.4, 6.0 Hz), 6.28 (1H, s), 7.14 (1H, dd, J=7.6, 1.2 Hz), 7.34 (1H, td, J=7.6, 1.2 Hz), 7.42 (1H, td, J=7.6, 2.0 Hz), 7.62 (1H, dd, J=7.6, 2.0 Hz), 12.19 (1H, s); $^{13}$C-NMR (100 MHz CDCl$_3$) δ:20.85, 20.88, 27.01, 30.85, 42.52, 74.30, 102.19, 106.02, 113.30, 115.09, 122.95, 126.53, 127.10, 129.82, 135.06, 147.64, 156.64, 159.94, 161.21, 168.24, 169.06, 197.05; IR (neat): 1771, 1653, 1635, 1587, 1558, 1505, 1436, 1373, 1270, 1192, 1178, 1138, 1083, 1055 cm$^{-1}$; mp: 104-106° C.

Acetic acid 2-(3-acetoxy-phenyl)-6-allyl-5-hydroxy-4-oxo-chroman-7-yl ester (9c)

$^1$H-NMR (400 MHz CDCl$_3$) δ:2.28 (3H, s), 2.30 (3H, s), 2.87 (1H, dd, J=17.2, 3.2 Hz), 3.07 (1H, dd, J=17.2, 13.2 Hz), 3.26 (2H, d, J=6.0 Hz), 4.98 (1H, dd, J=9.6, 1.6 Hz), 5.00 (1H, dd, J=17.2, 1.6 Hz), 5.43 (1H, dd, J=13.2, 3.2 Hz), 5.83 (1H, ddt, J=17.2, 9.6, 6.0 Hz), 6.30 (1H, s), 7.11 (1H, d, J=8.0 Hz), 7.20 (1H, s), 7.28 (1H, d, J=8.0 Hz), 7.42 (1H, t, J=8.0 Hz), 12.14 (1H, s); $^{13}$C-NMR (100 MHz CDCl$_3$) δ:20.89, 21.06, 27.03, 43.61, 78.38, 102.23, 106.06, 113.24, 115.08, 119.29, 122.05, 123.27, 129.88, 135.09, 139.77, 150.92, 156.69, 159.78, 161.19, 168.26, 169.27, 196.84; IR (neat): 1768, 1652, 1640, 1635, 1586, 1436, 1371, 1198, 1138 cm$^{-1}$; mp: 71-73° C.

Acetic acid 6-allyl-2-(2,6-diacetoxy-phenyl)-5-hydroxy-4-oxo-chroman-7-yl ester (9d)

$^1$H-NMR (400 MHz CDCl$_3$) δ: 2.25 (6H, s), 2.29 (3H, s), 2.71 (1H, dd, J=17.2, 3.2 Hz), 3.27 (2H, d, J=6.4 Hz), 3.56 (1H, dd, J=17.2, 14.0 Hz), 5.00 (1H, dd, J=10.4, 1.2 Hz), 5.03 (1H, dd, J=17.2, 1.2 Hz), 5.59 (1H, dd, J=14.0, 3.2 Hz), 5.85 (1H, ddt, J=17.2, 10.4, 6.4 Hz), 6.22 (1H, s), 7.05 (2H, d, J=8.0 Hz), 7.44 (1H, t, J=8.0 Hz), 12.23 (1H, s); $^{13}$C-NMR (100 MHz CDCl$_3$) δ:20.84, 27.08, 40.43, 72.23, 101.93, 105.79, 113.47, 115.19, 121.48, 122.48, 130.01, 135.04, 149.28, 156.77, 159.66, 161.36, 168.20, 168.96, 197.69; IR (neat): 1771, 1653, 1646, 1635, 1616, 1558, 1507, 1436, 1192, 1139 cm$^{-1}$; mp: 72-74° C.

Acetic acid 2-acetoxy-5-(7-acetoxy-6-allyl-5-hydroxy-4-oxo-chroman-2-yl)-phenyl ester (9e)

$^1$H-NMR (400 MHz CDCl$_3$) δ:2.28 (3H, s), 2.29 (3H, s), 2.29 (3H, s), 2.87 (1H, dd, J=17.2, 3.2 Hz), 3.05 (1H, dd, J=17.2, 13.6 Hz), 3.26 (2H, d, J=6.4 Hz), 4.98 (1H, d, J=9.2 Hz), 4.99 (1H, d, J=17.2 Hz), 5.41 (1H, dd, J=13.6, 3.2 Hz), 5.83 (1H, ddt, J=17.2, 9.2, 6.4 Hz), 6.29 (1H, d, J=2.4 Hz), 7.23 (1H, d, J=6.0 Hz), 7.24 (1H, d, J=2.4 Hz), 7.30 (1H, d, J=6.0 Hz), 12.13 (1H, s); $^{13}$C-NMR (100 MHz CDCl$_3$) δ:20.57, 20.59, 20.89, 27.03, 43.60, 78.01, 102.21, 106.04, 113.35, 115.10, 121.30, 123.87, 124.07, 135.07, 136.86, 142.26, 142.30, 156.72, 159.69, 161.21, 168.04, 168.08, 168.24, 196.69; IR (neat): 1769, 1751, 1653, 1647, 1637, 1507, 1436, 1374, 1262, 1216, 1201, 1137, 1115 cm$^{-1}$; mp: 97-99° C.

Under an Ar atmosphere, an olefin (7.09 mmol) and Grubbs catalyst, 2nd Generation (0.018 mmol) were sequentially added to a solution of (9a) to (9e) (0.36 mmol) in benzene (5 mL) at room temperature, and heated at 100° C. for 12 hours in a sealed tube. Heating was performed. After cooling, the solvent was distilled off, and the obtained residue was purified by silica gel column chromatography (hexane:EtOAc=40:1 (volume ratio)) (Rf value=0.40 by thin-layer chromatography) to obtain yellow crystals (10a) to (10e) and (10b').

The physical properties of the obtained intermediate Compounds (10a) to (10e) and (10b') were as follows.

Acetic acid 2-[5-hydroxy-6-(3-methyl-but-2-enyl)-4-oxo-chroman-2-yl]-phenyl Ester (10a)

$^1$H-NMR (400 MHz CDCl$_3$) δ:1.64 (3H, s), 1.68 (3H, s), 2.22 (3H, s), 2.77 (1H, dd, J=17.2, 3.2 Hz), 3.04 (1H, dd, J=17.2, 13.2 Hz), 3.20 (2H, d, J=7.6 Hz), 5.21 (1H, td, J=7.6, 2.8 Hz), 5.46 (1H, dd, J=13.2, 3.2 Hz), 6.36 (1H, d, J=8.0 Hz), 7.07 (1H, d, J=8.0 Hz), 7.19 (1H, d, J=8.0 Hz), 7.27 (1H, t, J=8.0 Hz), 7.34 (1H, td, J=8.0, 1.2 Hz), 7.56 (1H, dd, J=8.0, 1.2 Hz), 11.91 (1H, s); $^{13}$C-NMR (100 MHz CDCl$_3$) δ:17.47, 20.93, 25.76, 26.83, 42.87, 74.30, 106.76, 107.63, 121.74, 122.12, 123.00, 126.55, 127.21, 129.74, 130.40, 133.15, 138.22, 147.73, 159.37, 159.48, 169.08, 198.06; IR (neat): 1762, 1653, 1645, 1635, 1558, 1490, 1461, 1436, 1368, 1231, 1207, 1186, 1056, 790 cm$^{-1}$; mp: 93-95° C.

Acetic acid 2-[7-acetoxy-5-hydroxy-6-(3-methyl-but-2-enyl)-4-oxo-chroman-2-yl]-phenyl Ester (10b)

$^1$H-NMR (400 MHz CDCl$_3$) δ:1.64 (3H, s), 1.68 (3H, s), 2.28 (6H, s), 2.81 (1H, dd, J=17.2, 3.2 Hz), 3.08 (1H, dd, J=17.2, 13.2 Hz), 3.19 (2H, d, J=7.2 Hz), 5.09 (1H, t, J=7.2 Hz), 5.53 (1H, dd, J=13.2, 3.2 Hz), 6.23 (1H, s), 7.12 (1H, d, J=7.2 Hz), 7.32 (1H, t, J=7.2 Hz), 7.40 (1H, td, J=7.2, 1.6 Hz), 7.59 (1H, dd, J=7.2, 1.6 Hz), 12.16 (1H, s); $^{13}$C-NMR (100 MHz CDCl$_3$) δ:17.73, 20.85, 20.89, 21.95, 25.65, 42.58, 74.28, 102.06, 106.10, 115.20, 121.18, 122.97, 126.54, 127.13, 129.81, 130.10, 132.19, 147.68, 156.41, 159.61, 161.25, 168.34, 169.08, 197.08; IR (neat): 1771, 1683, 1653, 1646, 1635, 1558, 1540, 1506, 1490, 1456, 1436, 1373, 1195, 1139 cm$^{-1}$; mp: 73-75° C.

Acetic acid 2-(2-acetoxy-phenyl)-6-(3-methyl-pent-2-enyl)-5-hydroxy-4-oxo-chroman-7-yl Ester (10b')

$^1$H-NMR (400 MHz CDCl$_3$) δ:0.94 (3H, t, J=7.2 Hz), 1.03 (3H, t, J=7.2 Hz), 2.00 (2H, q, J=7.2 Hz), 2.18 (2H, q, J=7.2 Hz), 2.22 (3H, s), 2.30 (3H, s), 2.84 (1H, dd, J=17.2, 3.2 Hz), 3.10 (1H, dd, J=17.2, 13.6 Hz), 3.25 (2H, d, J=6.8 Hz), 5.04 (1H, t, J=6.8 Hz), 5.55 (1H, dd, J=13.6, 3.2 Hz), 6.25 (1H, s), 7.14 (1H, d, J=7.6, 1.2 Hz), 7.34 (1H, td, J=7.6, 1.2 Hz), 7.42 (1H, td, J=7.6, 2.0 Hz), 7.61 (1H, dd, J=7.6, 2.0 Hz), 12.18 (1H, s); $^{13}$C-NMR (100 MHz CDCl$_3$)

δ:12.59, 13.07, 20.90, 20.94, 21.39, 23.27, 29.05, 42.65, 74.30, 102.12, 106.15, 115.45, 119.21, 122.98, 126.58, 127.15, 129.84, 130.15, 143.46, 147.70, 156.56, 159.65, 161.29, 168.36, 169.11, 197.11; IR (neat): 1771, 1768, 1762, 1653, 1646, 1635, 1558, 1506, 1490, 1457, 1437, 1368, 1207, 1197, 1141, 1100, 1062 cm$^{-1}$; mp: 83-85° C.

Acetic acid 2-(3-acetoxy-phenyl)-5-hydroxy-6-(3-methyl-but-2-enyl)-4-oxo-chroman-7-yl Ester (10c)

$^1$H-NMR (400 MHz CDCl$_3$) δ:1.68 (3H, s), 1.75 (3H, s), 2.30 (3H, s), 2.32 (3H, s), 2.88 (1H, dd, J=17.2, 3.2 Hz), 3.07 (1H, dd, J=17.2, 13.2 Hz), 3.21 (2H, d, J=7.2 Hz), 5.11 (1H, td, J=7.2, 1.2 Hz), 5.43 (1H, dd, J=13.2; 3.2 Hz), 6.29 (1H, s), 7.13 (1H, dd, J=8.0, 1.2 Hz), 7.21 (1H, t, J=1.2 Hz), 7.29 (1H, d, J=8.0 Hz), 7.44 (1H, t, J=8.0 Hz), 12.14 (1H, s); $^{13}$C-NMR (100 MHz CDCl$_3$) δ:17.73, 20.87, 21.07, 21.96, 25.65, 43.66, 78.34, 102.06, 106.13, 115.15, 119.29, 121.21, 122.02, 123.27, 129.87, 132.19, 139.86, 150.93, 156.45, 159.43, 161.20, 168.34, 169.27, 196.84; IR (neat): 1768, 1635, 1587, 1433, 1371, 1202, 1171, 1137, 1066 cm$^{-1}$; mp: 84-86° C.

Acetic acid 2-(2,6-diacetoxy-phenyl)-5-hydroxy-6-(3-methyl-but-2-enyl)-4-oxo-chroman-7-yl Ester (10d)

$^1$H-NMR (400 MHz CDCl$_3$) δ:1.68 (3H, s), 1.75 (3H, s), 2.24 (6H, s), 2.29 (3H, s), 2.70 (1H, dd, J=17.2, 3.2 Hz), 3.20 (2H, d, J=7.6 Hz), 3.54 (1H, dd, J=17.2, 14.0 Hz), 5.10 (1H, t, J=7.6 Hz), 5.57 (1H, dd, J=14.0, 3.2 Hz), 6.19 (1H, s), 7.05 (2H, d, J=8.0 Hz), 7.43 (1H, t, J=8.0 Hz), 12.21 (1H, s); $^{13}$C-NMR (100 MHz CDCl$_3$) δ:17.71, 20.79, 20.83, 21.96, 25.65, 40.47, 72.20, 101.80, 105.85, 115.29, 121.09, 121.47, 122.51, 129.97, 132.25, 149.27, 156.50, 159.32, 161.36, 168.27, 168.97, 197.09; IR (neat): 1771, 1653, 1646, 1635, 1616, 1558, 1506, 1472, 1465, 1436, 1373, 1192, 1138, 1032 cm$^{-1}$; mp: 68-70° C.

Acetic acid 2-(3,4-diacetoxy-phenyl)-5-hydroxy-6-(3-methyl-but-2-enyl)-4-oxo-chroman-7-yl Ester (10e)

$^1$H-NMR (400 MHz CDCl$_3$) δ:1.66 (3H, s), 1.73 (3H, s), 2.28 (6H, s), 2.29 (3H, s), 2.86 (1H, dd, J=17.2, 3.2 Hz), 3.04 (1H, dd, J=17.2, 13.6 Hz), 3.19 (2H, d, J=7.6 Hz), 5.09 (1H, tt, J=7.6, 1.2 Hz), 5.40 (1H, dd, J=13.6, 3.2 Hz), 6.26 (1H, s), 7.23 (1H, d, J=8.0 Hz), 7.24 (1H, s), 7.29 (1H, d, J=8.0 Hz), 12.11 (1H, s); $^{13}$C-NMR (100 MHz CDCl$_3$) δ:17.73, 20.57, 20.59, 20.87, 21.96, 25.65, 43.64, 77.95, 102.05, 106.09, 115.23, 121.18, 121.28, 123.85, 124.06, 132.20, 136.93, 142.23, 142.29, 156.45, 159.33, 161.21, 168.05, 168.09, 168.34, 196.68; IR (neat): 1772, 1654, 1646, 1635, 1507, 1430, 1374, 1270, 1205, 1197, 1138 cm$^{-1}$; mp: 121-123° C.

Under an Ar atmosphere, K$_2$CO$_3$ (0.86 mmol) was added to a solution of (10a) to (10e) and (10b')(0.29 mmol) in MeOH (2 mL) at room temperature, and the mixture was stirred at room temperature for 30 minutes. After completion of the reaction, 10% HCl (aq.) (1 mL) was added, it was extracted with EtOAc (3 mL×5), dried over MgSO$_4$, and the solvent was distilled off. The obtained residue was purified by silica gel column chromatography (hexane:EtOAc=10:1 (volume ratio)) (Rf value=0.20 by thin-layer chromatography), and yellow crystalline Compounds-33 to 34, 36, 42 to 43 and 45 were obtained.

The physical properties of the obtained intermediate Compounds-33 to 34, 36, 42 to 43 and 45 were as follows.

5,7-dihydroxy-2-(2-hydroxy-phenyl)-6-(3-methyl-but-2-enyl)-chroman-4-one (Compound-33)

$^1$H-NMR (400 MHz Acetone-d6) δ:1.63 (3H, s), 1.74 (3H, s), 2.81 (1H, dd, J=17.2, 3.2 Hz), 3.08 (1H, dd, J=17.2, 13.2 Hz), 3.24 (2H, d, J=7.2 Hz), 5.23 (1H, tt, J=7.2, 1.2 Hz), 5.77 (1H, dd, J=13.2, 3.2 Hz), 6.08 (1H, s), 6.92 (1H, t, J=7.6 Hz), 6.93 (1H, d, J=7.6 Hz), 7.20 (1H, t, J=7.6 Hz), 7.51 (1H, d, J=7.6 Hz), 12.47 (1H, s); $^{13}$C-NMR (100 MHz Acetone-d6) δ:17.80, 21.59, 25.82, 42.55, 75.24, 95.27, 103.01, 109.01, 116.22, 120.60, 123.52, 126.41, 127.60, 130.08, 131.18, 154.74, 162.13, 162.24, 164.72, 197.37; IR (neat): 1653, 1635, 1616, 1601, 1576, 1558, 1540, 1506, 1496, 1490, 1472, 1457, 1339, 1312, 1272, 1155, 1083, 751 cm$^{-1}$; mp: 174-176° C.

5,7-dihydroxy-2-(3-hydroxy-phenyl)-6-(3-methyl-but-2-enyl)-chroman-4-one (Compound-34)

$^1$H-NMR (400 MHz Acetone-d6) δ:1.63 (3H, s), 1.74 (3H, s), 2.77 (1H, dd, J=17.2, 2.8 Hz), 3.10 (1H, dd, J=17.2, 12.8 Hz), 3.34 (2H, d, J=7.2 Hz), 5.22 (1H, td, J=7.2, 1.2 Hz), 5.46 (1H, dd, J=12.8, 2.8 Hz), 6.06 (1H, s), 6.84 (1H, d, J=8.0 Hz), 6.99 (1H, d, J=8.0 Hz), 7.02 (1H, s), 7.24 (1H, t, J=8.0 Hz), 12.43 (1H, s); $^{13}$C-NMR (100 MHz Acetone-d6) δ:17.06, 20.83, 25.09, 42.92, 78.94, 94.56, 102.33, 108.33, 113.33, 115.45, 117.45, 122.73, 129.78, 130.48, 140.88, 157.67, 160.93, 161.45, 163.99, 196.14; IR (neat): 1635, 1589, 1485, 1455, 1327, 1305, 1283, 1182, 1166, 1155, 1085, 1076 cm$^{-1}$; mp: 179-181° C.

2-(3,4-dihydroxy-phenyl)-5,7-dihydroxy-6-(3-methyl-but-2-enyl)-chroman-4-one (Compound-36)

$^1$H-NMR (400 MHz Acetone-d6) δ:1.62 (3H, s), 1.73 (3H, s), 2.70 (1H, dd, J=17.2, 3.2 Hz), 3.11 (1H, dd, J=17.2, 12.8 Hz), 3.23 (2H, d, J=7.2 Hz), 5.22 (1H, t, J=7.2 Hz), 5.35 (1H, dd, J=12.8, 3.2 Hz), 6.01 (1H, s), 6.85 (2H, s), 7.01 (1H, s), 8.19 (1H, br) 12.45 (1H, s); $^{13}$C-NMR (100 MHz Acetone-d6) δ:17.79, 21.56, 25.81, 43.60, 79.82, 95.24, 103.04, 108.92, 114.65, 115.95, 119.17, 123.51, 131.18, 131.64, 145.94, 146.28, 161.88, 162.17, 164.70, 197.26; IR (neat): 1653, 1646, 1635, 1624, 1616, 1596, 1577, 1559, 1507, 1457, 1448, 1339, 1287, 1158, 1120, 1090 cm$^{-1}$; mp: 121-123° C.

2-(2,6-dihydroxy-phenyl)-5,7-dihydroxy-6-(3-methyl-but-2-enyl)-chroman-4-one (Compound-42)

$^1$H-NMR (400 MHz Acetone-d6) δ:1.63 (3H, s), 1.74 (3H, s), 2.51 (1H, dd, J=17.2, 3.2 Hz), 3.24 (2H, d, J=7.2 Hz), 3.89 (1H, dd, J=17.2, 14.0 Hz), 5.23 (1H, t, J=7.2 Hz), 6.00 (1H, s), 6.01 (1H, dd, J=14.0, 3.2 Hz), 6.46 (2H, d, J=8.0 Hz), 7.02 (1H, t, J=8.0 Hz), 8.57 (2H, s), 12.58 (1H, s); $^{13}$C-NMR (100 MHz Acetone-d6) δ:17.79, 21.59, 25.82, 40.52, 73.38, 95.22, 103.03, 108.39, 108.84, 111.73, 123.62, 130.88, 131.09, 157.74, 162.39, 162.59, 164.51, 198.39; IR (neat): 1653, 1635, 1603, 1559, 1506, 1472, 1456, 1451, 1447, 1309, 1150 cm$^{-1}$; mp: 244-246° C.

5-hydroxy-2-(2-hydroxy-phenyl)-6-(3-methyl-but-2-enyl)-chroman-4-one (Compound-43)

$^1$H-NMR (400 MHz Acetone-d6) δ:1.70 (6H, s), 2.93 (1H, dd, J=17.2, 2.4 Hz), 3.18 (1H, dd, J=17.2, 12.8 Hz), 3.25

(2H, d, J=7.2 Hz), 5.29 (1H, tt, J=7.2, 1.2 Hz), 5.83 (1H, dd, J=12.8, 2.4 Hz), 6.47 (1H, d, J=8.0 Hz), 6.92 (1H, t, J=8.0 Hz), 6.94 (1H, d, J=8.0 Hz), 7.21 (1H, t, J=8.0 Hz), 7.31 (1H, d, J=8.0 Hz), 7.54 (1H, dd, J=8.0, 1.2 Hz), 8.77 (1H, s), 12.15 (1H, s); $^{13}$C-NMR (100 MHz Acetone-d6) δ:17.75, 25.82, 27.37, 43.07, 75.31, 107.57, 108.45, 116.26, 120.68, 121.93, 123.05, 126.30, 127.62, 130.17, 132.98, 138.73, 154.73, 160.18, 161.03, 200.19; IR (neat): 1627, 1609, 1461, 1447, 1345, 1339, 1235, 1065, 735 cm$^{-1}$; mp: 172-174° C.

6-(3-ethyl-pent-2-enyl)-5,7-dihydroxy-2-(2-hydroxyphenyl)-chroman-4-one (Compound-45)

$^1$H-NMR (400 MHz Acetone-d6) δ:0.94 (3H, t, J=7.2 Hz), 1.01 (3H, t, J=7.2 Hz), 1.98 (2H, q, J=7.2 Hz), 2.24 (2H, q, J=7.2 Hz), 2.82 (1H, dd, J=17.2, 3.2 Hz), 3.08 (1H, dd, J=17.2, 12.8 Hz), 3.29 (2H, d, J=7.2 Hz), 5.21 (1H, t, J=7.2 Hz), 5.77 (1H, dd, J=12.8, 3.2 Hz), 6.08 (1H, s), 6.91 (1H, t, J=7.6 Hz), 6.94 (1H, d, J=7.6 Hz), 7.20 (1H, td, J=7.6, 1.2 Hz), 7.52 (1H, dd, J=7.6, 1.2 Hz), 8.77 (1H, s), 9.62 (1H, s), 12.49 (1H, s); $^{13}$C-NMR (100 MHz Acetone-d6) δ:13.11, 13.47, 21.01, 23.62, 42.57, 75.26, 95.31, 103.07, 109.14, 116.25, 120.64, 121.55, 126.44, 127.64, 130.11, 142.61, 154.75, 162.17, 162.31, 164.73, 197.41; IR (neat): 2964, 1653, 1635, 1616, 1595, 1559, 1507, 1496, 1490, 1472, 1457, 1339, 1309, 1302, 1272, 1156, 1082, 752 cm$^{-1}$; mp: 154-156° C.

REFERENCES

1) Sandra Tischer and Peter Metz, Adv. Synth. Catal. 2007, 349, 147-151.
2) Belanger, Patrice C., Scheigetz, John and Rokach, Joshua, Eur. Pat. Appl., 165810, 27 Dec. 1985.

The compounds described below were prepared or obtained in the following manner.
8-Prenylnaringenin
8-Prenylnaringenin was purchased from Sigma-Aldrich Corporation (St. Louis, Mo.).
DMSO was used as a solvent for dissolving 8-prenylnaringenin.

Example 1 Measurement of Inhibitory Effect of 6-Prenylnaringenin on T-Type Calcium Channel by Whole-Cell Patch Clamp Method Using a human kidney cell-derived cell line, an EK293 cell, in which a human T-type calcium channel was forcibly expressed, the inhibitory effect of 6-prenylnaringenin on the T-type calcium channel was measured by the whole cell patch clamp method.

In the whole-cell patch clamp method, the following solutions are used as an external solution and an internal solution, the holding potential is set to −80 mV, and the barium current was measured as an inward current flow upon a potential jump from −80 mV to −20 mV. Here, in order to eliminate the influence of the high threshold activated-calcium channel, a value obtained by subtracting the current at 150 ms after the start of stimulation from the peak current was used as a T-channel current (T-current) for data analysis.
External Solution Composition
Aqueous solution containing the following:
97 mM N-methyl-D-glucamine (NMDG);
10 mM BaCl$_2$;
10 mM 4-(2-hydroxyethyl)-1-piperazine ethanesulfonic acid (HEPES);
40 mM tetraethylammonium chloride (TEA-Cl); and
5 mM glucose
(pH 7.4).
Internal Solution Composition
Aqueous solution containing the following:
4 mM MgCl$_2$;
140 mM CsCl;
10 mM HEPES; and
5 mM glycol ether diamine tetraacetic acid (EGTA)
(pH 7.2).

Data obtained from the above-described experiment is shown in the table below.

TABLE 1

| Compound concentration (nM) | Inhibition rate (%) | Number of cases |
| --- | --- | --- |
| 300 | 0 | 6 |
| 1000 | 82.7 | 6 |
| 3000 | 99.0 | 6 |

Figure 1:
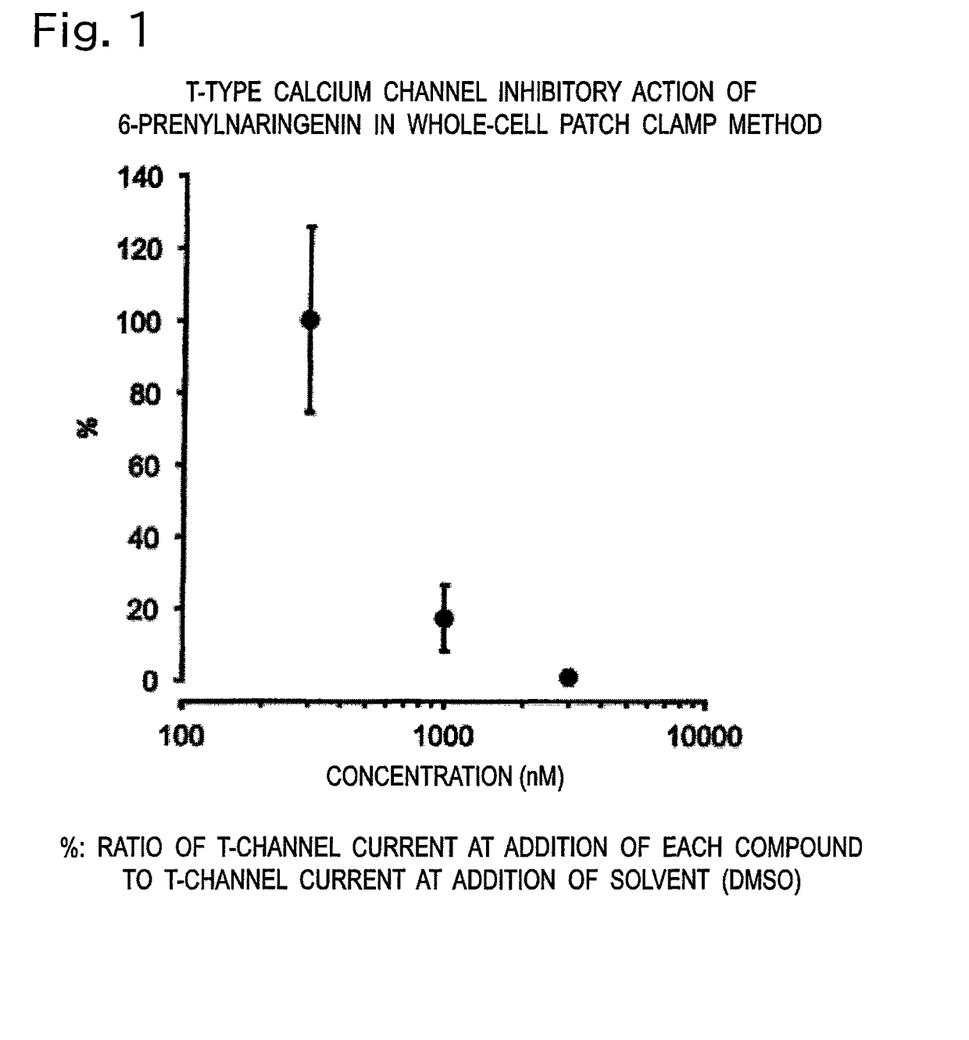
FIG. 1 is a graph chart showing experimental results of Example 1.
Figure 2:
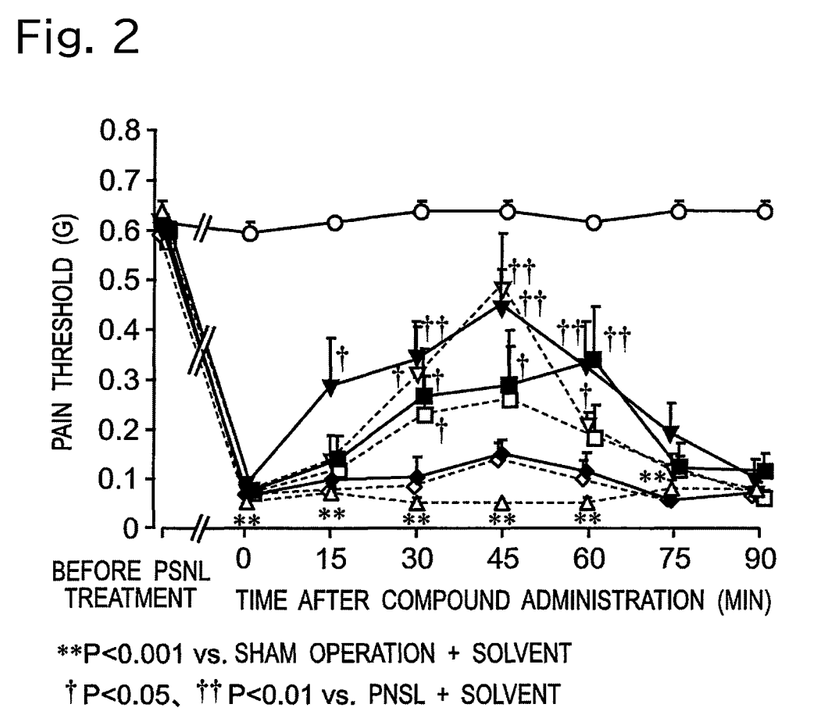
Figure 3:
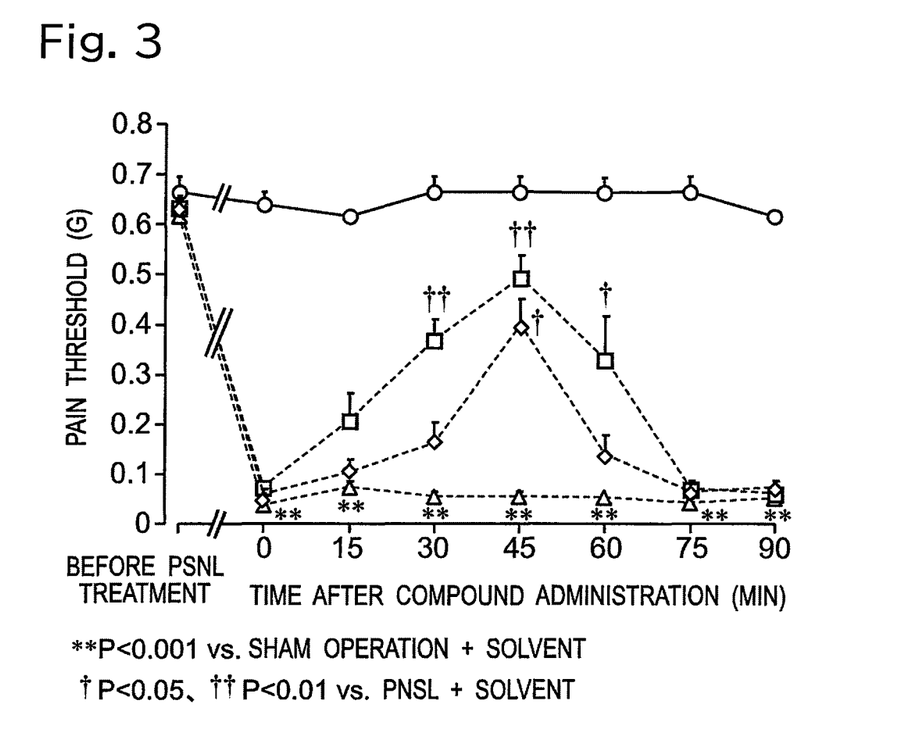
FIG. 3 is a graph chart showing the inhibitory action of Compound-41 on PSNL-induced hyperalgesia. Open circles show a result of vehicle administration after sham operation, open upward triangles show a result of vehicle administration after PSNL-induced hyperalgesia, open diamonds show a result of Compound-41 10 mg/kg administration after PSNL-induced hyperalgesia, and open squares show a result of Compound-41 20 mg/kg administration after PSNL-induced hyperalgesia.
Figure 4:
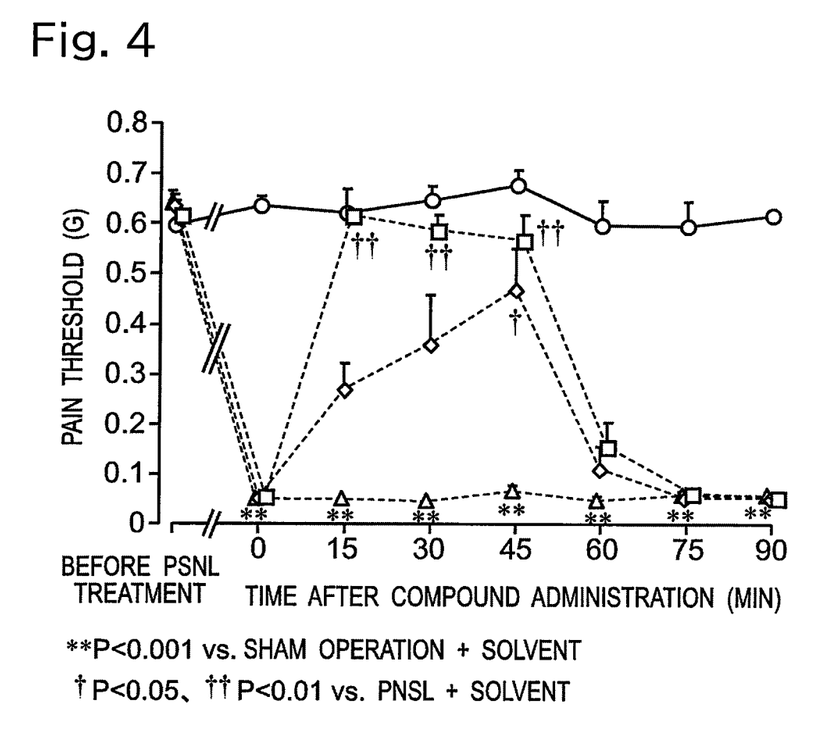
FIG. 4 is a graph chart showing the inhibitory action of Compound-45 on PSNL-induced hyperalgesia. Open circles show a result of vehicle administration after sham operation, open upward triangles show a result of vehicle administration after PSNL-induced hyperalgesia, open diamonds show a result of Compound-45 10 mg/kg administration after PSNL-induced hyperalgesia, and open squares show a result of Compound-45 20 mg/kg administration after PSNL-induced hyperalgesia.
Figure 5:
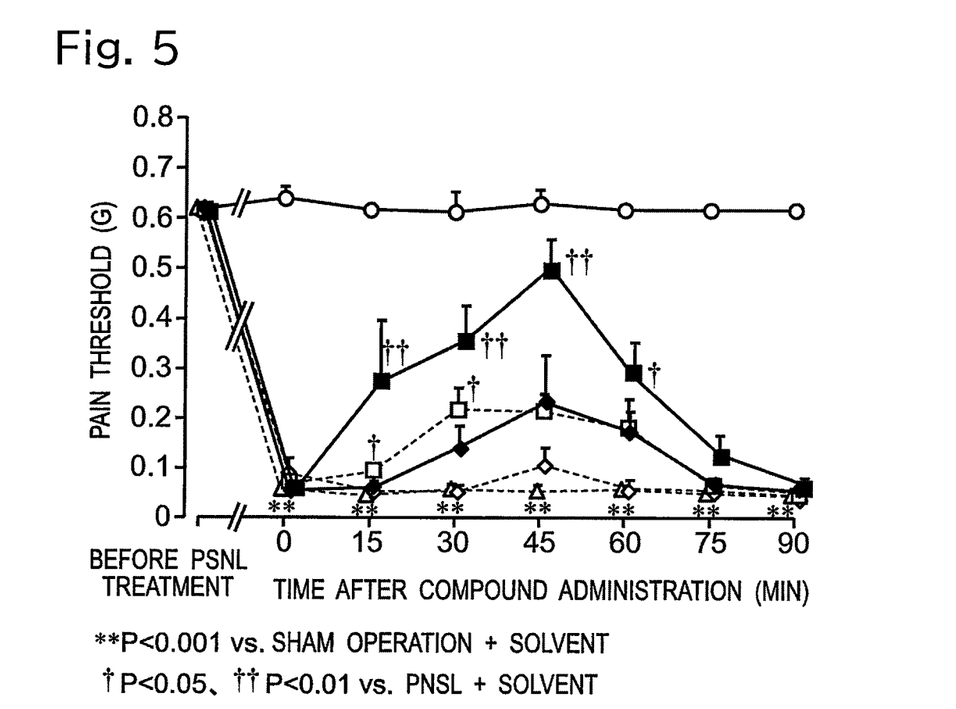
FIG. 5 is a graph chart showing the inhibitory action of Compound-47 on PSNL-induced hyperalgesia. Open circles show a result of vehicle administration after sham operation, open upward triangles show a result of vehicle administration after PSNL-induced hyperalgesia, open diamonds show a result of 6-prenylnaringenin 10 mg/kg administration after PSNL-induced hyperalgesia, open squares show a result of 6-prenylnaringenin 20 mg/kg administration after PSNL-induced hyperalgesia, solid diamonds show a result of Compound-47 10 mg/kg administration after PSNL-induced hyperalgesia, and solid squares show Compound-47 20 mg/kg administration after PSNL-induced hyperalgesia.

Data obtained from the above-described experiment are shown in FIG. 1. In FIG. 1, the data are shown as a ratio (%) of a T-current at addition of a compound to a T-current at addition of a solvent (DMSO).

The IC50 value (nM) of 6-Prenylnaringenin in Example 1 is shown in the table below. This IC50 value is a value calculated by GraphPad Prism® (GraphPad Software, Inc.) using the results of Example 1.

TABLE 2

| | IC50 (nM) |
| --- | --- |
| 6-Prenylnaringenin | 800.9 |

From the above example, it was confirmed that 6-prenylnaringenin has an excellent T-type calcium channel inhibitory action.

Example 2 T-Type Calcium Channel Inhibitory Action of Each Compound in Whole-Cell Patch Clamp Method The inhibitory effect of the compound of the present invention on the T-type calcium channel was measured in the same manner as in Example 1, except that the compound of the present invention was used instead of 6-prenylnaringenin.

The IC50 value of each compound obtained by the experiment is shown in the following table as a percentage with respect to the IC50 value of 6-prenylnaringenin.

TABLE 3

| Compound name | Ratio of IC50 value to IC50 value of 6-prenylnaringenin (%) |
| --- | --- |
| Compound-33 | 12.2 |
| Compound-34 | 12.5 |
| Compound-36 | 87.5 |
| Compound-39 | 10.6 |
| Compound-40 | 7.7 |
| Compound-41 | 9.0 |
| Compound-42 | 72.3 |
| Compound-43 | 26.6 |
| Compound-45 | 2.3 |
| Compound-46 | 15.0 |

TABLE 3-continued

| Compound name | Ratio of IC50 value to IC50 value of 6-prenylnaringenin (%) |
|---|---|
| Compound-47 | 8.1 |
| Compound-48 | 54.8 |

The above examples show that the compounds of the present invention have a more excellent T-type calcium channel inhibitory action than 6-prenylnaringenin.

Formulation Example 1

A granule containing the T-type calcium channel inhibitor according to the present invention was produced in accordance with the following procedure.

TABLE 4

| 6-Prenylnaringenin | 10 mg |
|---|---|
| Lactose | 700 mg |
| Corn starch | 274 mg |
| HPC-L | 16 mg |
| Total | 1000 mg |

Each compound of the present invention and lactose were put through a 60-mesh screen, and corn starch was put through a 120-mesh screen. They were mixed by a V-type mixer. To the mixed powder was added an aqueous solution of low-viscosity hydroxypropyl cellulose (HPC-L), and the mixture was kneaded. The obtained product was granulated (extrusion granulation, pore diameter: 0.5 to 1 mm), and then dried. The obtained dry grains were sieved by a vibrating screen (12/60 mesh) to obtain a granule.

Formulation Example 2

An intravenous preparation containing the T-type calcium channel inhibitor of the present invention was produced in accordance with the following procedure.

TABLE 5

| Each Compound of the present invention | 100 mg |
|---|---|
| Saturated fatty acid glyceride | 1000 ml |

The solution of the above components is normally intravenously administered to a patient at a rate of 1 ml per minute.

Example 3 Effects of Each Compound on Partial Sciatic Nerve Ligation (PSNL)-Induced Hyperalgesia In Example 2, Compounds-40, 41, 45 and 47, which exhibited excellent T-type calcium channel inhibitory activity in vitro, were examined for their inhibitory activity against PSNL-induced hyperalgesia. PSNL-induced hyperalgesia was performed using ddY male mice under inhaled isoflurane anesthesia by incising the skin on the femur of the mouse and exposing ⅓ to ½ of the exposed sciatic nerve was completely ligated with a 8-0 suture. In addition, mice were treated until the sciatic nerve was exposed, and mice that did not ligate the exposed sciatic nerve were designated as Sham group (sham operation). The pain threshold was measured by the von Frey method.

Compounds-40, 41, 45 and 47 were suspended in 5% aqueous carboxymethylcellulose and administered intraperitoneally using mice after 7 days of PSNL treatment, which is considered to be a chronic phase in which hyperalgesia is stable, and Pain thresholds were measured every minute. As controls, a group to which a solvent was administered after sham operation and a group to which a solvent and 6-prenylnaringenin were administered after induction of hyperalgesia by PNSL were provided.

The results are shown in FIGS. 2-5.

In the groups where Compounds 40, 41, 45, and 47 received at a dose of 10 to 30 mg/kg, the pain threshold approached the vehicle-administered group after sham operation, which did not induce hyperalgesia, than the vehicle-administered group after PSNL treatment, significantly suppressed hyperalgesia, and its effect was observed for 15 to 60 minutes after administration.

INDUSTRIAL APPLICABILITY

The T-type calcium channel inhibitor of the present invention which is a flavanone compound has an excellent T-type calcium channel inhibitory action. The T-type calcium channel inhibitor of the present invention is very useful in the fields of, for example, medical cares, pharmaceutical products and prophylactic agents.

The invention claimed is:

1. A compound selected from the group consisting of:
   5,7-dihydroxy-2-(2-hydroxy-phenyl)-6-(3-methyl-but-2-enyl)-chroman-4-one (Compound-33);
   5,7-dihydroxy-2-(3-hydroxy-phenyl)-6-(3-methyl-but-2-enyl)-chroman-4-one (Compound-34);
   5,7-dihydroxy-2-(4-hydroxy-phenyl)-6-(3-methyl-butyl)-chroman-4-one (Compound-39);
   6-(3-ethyl-pent-2-enyl)-5,7-dihydroxy-2-(4-hydroxy-phenyl)-chroman-4-one (Compound-40);
   6-(2-cyclopentylidene-ethyl)-5,7-dihydroxy-2-(4-hydroxy-phenyl)-chroman-4-one (Compound-41);
   2-(2,6-dihydroxy-phenyl)-5,7-dihydroxy-6-(3-methyl-but-2-enyl)-chroman-4-one (Compound-42);
   5-hydroxy-2-(2-hydroxy-phenyl)-6-(3-methyl-but-2-enyl)-chroman-4-one (Compound-43);
   6-(3-ethyl-pent-2-enyl)-5,7-dihydroxy-2-(2-hydroxy-phenyl)-chroman-4-one (Compound-45);
   6-(3-ethyl-pentyl)-5,7-dihydroxy-2-(4-hydroxy-phenyl)-chroman-4-one (Compound-46);
   6-(2-cyclopentyl-ethyl)-5,7-dihydroxy-2-(4-hydroxy-phenyl)-chroman-4-one (Compound-47); and
   5,7-dihydroxy-2-(4-hydroxy-phenyl)-6-(3-propyl-hex-2-enyl)-chroman-4-one (Compound-48)
   or the pharmaceutically acceptable salt thereof.

2. The compound according to claim 1, selected from the group consisting of:
   6-(3-ethyl-pent-2-enyl)-5,7-dihydroxy-2-(4-hydroxy-phenyl)-chroman-4-one (Compound-40);
   6-(2-cyclopentylidene-ethyl)-5,7-dihydroxy-2-(4-hydroxy-phenyl)-chroman-4-one (Compound-41);
   6-(3-ethyl-pent-2-enyl)-5,7-dihydroxy-2-(2-hydroxy-phenyl)-chroman-4-one (Compound-45); and
   6-(2-cyclopentyl-ethyl)-5,7-dihydroxy-2-(4-hydroxy phenyl)-chroman-4-one (Compound-47)
   or the pharmaceutically acceptable salt thereof.

3. A pharmaceutical composition for inhibiting a T-type calcium channel, comprising the compound according to claim 1 or a pharmaceutically acceptable salt thereof and a pharmaceutically acceptable carrier.

4. A therapeutic or prophylactic agent for treating a condition selected from the group consisting of epilepsy, hyperaldosteronemia, inflammation, edema, cardiac hypertrophy, heart failure, cardiomyopathy, atrial fibrillation, tachyarrhythmia, arteriosclerosis, nephritis, nephropathy or renal failure, comprising the compound according to claim 1 or a pharmaceutically acceptable salt thereof and a pharmaceutically acceptable carrier, wherein the agent inhibits a T-type calcium channel.

5. A therapeutic or prophylactic agent for treating neuropathic pains comprising the compound according to claim 1 or a pharmaceutically acceptable salt thereof and a pharmaceutically acceptable carrier, wherein the agent inhibits a T-type calcium channel.

6. A method for treating a condition selected from the group consisting of epilepsy, hyperaldosteronemia, inflammation, edema, cardiac hypertrophy, heart failure, cardiomyopathy, atrial fibrillation, tachyarrhythmia, arteriosclerosis, nephritis, nephropathy or renal failure, comprising administering the compound according to claim 1 or a pharmaceutically acceptable salt thereof, to a patient in need thereof, wherein the compound inhibits a T-type calcium channel.

7. A method for treating neuropathic pains, comprising administering the compound according to claim 1 or a pharmaceutically acceptable salt thereof, to a patient in need thereof, wherein the compound inhibits a T-type calcium channel.

8. A method for inhibiting a T-type calcium channel, comprising administrating a compound according to claim 1 or a pharmaceutically acceptable salt thereof to a subject in which the T-type calcium channel is to be inhibited.

* * * * *